United States Patent
Aoki et al.

(10) Patent No.: US 10,851,181 B2
(45) Date of Patent: Dec. 1, 2020

(54) POLYMER AND METHOD FOR PRODUCING POLYMER MEMBRANE

(71) Applicant: Panasonic Intellectual Property Management Co., Ltd., Osaka (JP)

(72) Inventors: Takahiro Aoki, Osaka (JP); Tomoko Kawashima, Osaka (JP); Yuko Taniike, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/507,067

(22) Filed: Jul. 10, 2019

(65) Prior Publication Data

US 2019/0330383 A1  Oct. 31, 2019

Related U.S. Application Data

(63) Continuation of application No. PCT/JP2017/042713, filed on Nov. 29, 2017.

(30) Foreign Application Priority Data

Jan. 23, 2017  (JP) .................. 2017-009592

(51) Int. Cl.
| | |
|---|---|
| *C08B 15/10* | (2006.01) |
| *B01D 67/00* | (2006.01) |
| *B01D 71/10* | (2006.01) |
| *C08B 11/193* | (2006.01) |
| *C08G 59/22* | (2006.01) |

(52) U.S. Cl.
CPC .......... *C08B 15/10* (2013.01); *B01D 67/0006* (2013.01); *B01D 67/0095* (2013.01); *B01D 71/10* (2013.01); *C08B 11/193* (2013.01); *C08G 59/22* (2013.01); *B01D 2323/30* (2013.01)

(58) Field of Classification Search
CPC ....... C08B 15/10; C08B 11/193; C08G 59/22; B01D 67/0095; B01D 71/10; B01D 67/0006; B01D 2323/30
USPC ......................................... 536/88
See application file for complete search history.

(56) References Cited

U.S. PATENT DOCUMENTS

| | | |
|---|---|---|
| 2002/0039629 A1 | 4/2002 | Inagaki et al. |
| 2004/0206694 A1 | 10/2004 | Charkoudian |
| 2005/0079361 A1 | 4/2005 | Hamed et al. |
| 2008/0245736 A1 | 10/2008 | Charkoudian et al. |
| 2016/0243521 A1 | 8/2016 | Hayashi et al. |
| 2016/0257941 A1 | 9/2016 | Villain et al. |
| 2016/0355662 A1 | 12/2016 | Tokuoka et al. |
| 2018/0056271 A1 | 3/2018 | Kawai et al. |

FOREIGN PATENT DOCUMENTS

| | | |
|---|---|---|
| CN | 104387609 | 3/2015 |
| JP | 3-068431 | 3/1991 |
| JP | 4-202895 | 7/1992 |
| JP | 5-237142 | 9/1993 |
| JP | 5-239263 | 9/1993 |
| JP | 9-137387 | 5/1997 |
| JP | 2860908 B2 | 2/1999 |
| JP | 11-315475 | 11/1999 |
| JP | 2002-086624 | 3/2002 |
| JP | 2004-155806 | 6/2004 |
| JP | 2004-314072 | 11/2004 |
| JP | 2008-043948 | 2/2008 |
| JP | 2011-116457 | 6/2011 |
| JP | 2015-137436 | 7/2015 |
| JP | 2016-160330 A | 9/2016 |
| JP | 2016-536114 | 11/2016 |
| KR | 10-2009-0025950 | 3/2009 |
| KR | 10-2009-0025974 | 3/2009 |
| WO | 2012/147255 | 11/2012 |
| WO | 2015/056681 | 4/2015 |
| WO | 2015/137170 | 9/2015 |
| WO | 2016/167268 | 10/2016 |

OTHER PUBLICATIONS

Capitani et al. (Macromolecules 2000, 33, 430-437).*
International Search Report of PCT application No. PCT/JP2017/042713 dated Feb. 20, 2018.
Sunkyu Park et al., "Cellulose crystallinity index: measurement techniques and their impact on interpreting cellulase performance", Biotechnology for Biofuels, May 24, 2010.
Hiroyuki Kono, "Characterization and properties of carboxymethyl cellulose hydrogels crosslinked by polyethylene glycol", Carbohydrate Polymers, vol. 106, Feb. 4, 2014, pp. 84-93.
He Liu et al., "Porous aerogels prepared by crosslinking of cellulose with 1,4-butanediol diglycidyl ether in NaOH/urea solution", RSC Advances, 2016, vol. 6(49), Apr. 2016, pp. 42854-42862.

(Continued)

*Primary Examiner* — Shaojia A Jiang
*Assistant Examiner* — Michael C Henry
(74) *Attorney, Agent, or Firm* — McDermott Will & Emery LLP

(57) ABSTRACT

In order to obtain a crosslinked cellulose without derivatization, a polymer according to an embodiment of the present disclosure is a polymer having a structure in which cellulose substantially represented by the following formula (c1) is crosslinked with a polyfunctional epoxy compound:

[Chemical Formula 1]

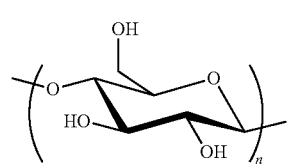

(c1)

wherein in the formula (c1), n represents an integer of 2 or more.

6 Claims, 16 Drawing Sheets

(56) References Cited

OTHER PUBLICATIONS

Wang Ai-ting et al., "Preparation of Porous Cellulosic Absorbing Materials", Linchan Huaxue Yu Gongye, 2015, vol. 35(6), pp. 1-7.
S. Z. Rogovina et al., "Solid state production of cellulose-chitosan blends and their modification with the diglycidyl ether of oligo(ethylene oxide)", Polymer Degradation and Stability, vol. 73(3), Dec. 2001, pp. 557-560.
Eli Ruckenstein et al., "Crosslinked mercerized cellulose membranes and their application to membrane affinity chromatography", Journal of Membrane Science, vol. 193(1), Jun. 2001, pp. 131-140.
The Extended European Search Report dated Dec. 5, 2019 for the related European Patent Application No. 17892402.3.
Communication pursuant to Article 94(3) EPC dated Sep. 16, 2020 for the related European Patent Application No. 17892402.3.
Airong Xu et al: "Dissolution Behavior of Cellulose in IL+ DMSO Solvent: Effect of Alkyl Length in Imidazolium Cation on Cellulose Dissolution", Advances in Materials Science and Engineering, vol. 2015, Jan. 1, 2015 (Jan. 1, 2015), pp. 1-4, XP055627996.
Jurgen Vitz et al: "Extended dissolution studies of cellulose in imidazolium based ionic liquids", RCS, Green Chemistry, Royal Society of Chemistry, GB, vol. 11, No. 3, Jan. 1, 2009 (Jan. 1, 2009), pp. 417-424, XP002659850.

\* cited by examiner

POLYMER AND METHOD FOR PRODUCING POLYMER MEMBRANE

BACKGROUND

1. Technical Field

The present disclosure relates to a polymer. The present disclosure also relates to a method for producing a polymer membrane.

2. Description of the Related Art

Conventionally, high water absorption resins have been utilized for sanitary goods such as paper diapers, water-retaining materials for gardening and the like. As high water absorption resins used for such purposes, sodium polyacrylate has been mainly used.

On the other hand, from the viewpoint of environmental loading reduction and the like, development of water absorbing materials that use naturally occurring polymers has been required. For example, PTL 1 listed below discloses a polymer obtained by crosslinking carboxymethyl cellulose (CMC) with ethylene glycol diglycidyl ether. PTL 2 listed below discloses production of crosslinked cellulose ether by a method including mixing an aqueous solution of an alkaline metal hydroxide as a catalyst with cellulose and adding polydiglycidyl ether as a cross-linking reagent and an etherificating agent. PTL 3 discloses a crosslinked cellulose composite semipermeable membrane and a method for producing the same.

CITATION LIST

Patent Literature

PTL 1: WO2012/147255
PTL 2: Japanese Patent Application Publication No. 2004-155806
PTL 3: Japanese Patent Application Publication No. H03-068431

Non-Patent Literature

NPL 1: Park et al., "Cellulose crystallinity index: measurement techniques and their impact on interpreting cellulase performance", Biotechnology for Biofuels, 2010, 3 10.
NPL 2: Hiroyuki Kono, "Characterization and properties of carboxymethyl cellulose hydrogels crosslinked by polyethylene glycol", Carbohydrate Polymers, 15 Jun. 2014, Volume 106, Pages 84-93.

SUMMARY

However, cellulose has been known to be difficult to be dissolved because of formation of intramolecular and intermolecular hydrogen bonds. Then, in PTL 1 and 2, derivatized cellulose has been used. By derivatization of cellulose, hydrogen bonds between cellulose molecular chains can be decreased, and therefore, it becomes possible to cause cellulose reaction with a cross-linking reagent efficiently. However, when cellulose is derivatized, the mechanical strength of the finally obtained crosslinked cellulose tends to be lowered. For example, even in a water absorption state, it has been difficult to obtain a sheet of crosslinked cellulose that is capable of maintaining a form as a sheet.

As an exemplary embodiment of the present disclosure, the following is provided.

A polymer having a structure in which cellulose substantially represented by the following general formula (I) is crosslinked with a polyfunctional epoxy compound:

[Chemical Formula 1]

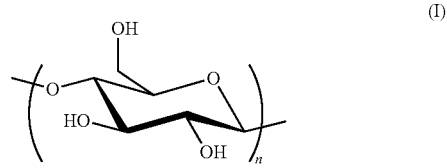

(I)

wherein in the general formula (I), n represents an integer of 2 or more.

A comprehensive or specific aspect may be realized by a polymer, a polymer membrane, a polymer sheet or a method. In addition, a comprehensive or specific aspect may be realized by any combination of a polymer, a polymer membrane, a polymer sheet and a method.

An additional effect and advantage of disclosed embodiments become clear from the specification and the drawings. Effects and/or advantages are individually provided by various embodiments or features disclosed in the specification and the drawings and not all are required for obtaining one or more of them.

According to an embodiment of the present disclosure, a crosslinked cellulose can be obtained without derivatization, for example, by using naturally occurring cellulose.

DESCRIPTION OF EMBODIMENTS

Figure 1:
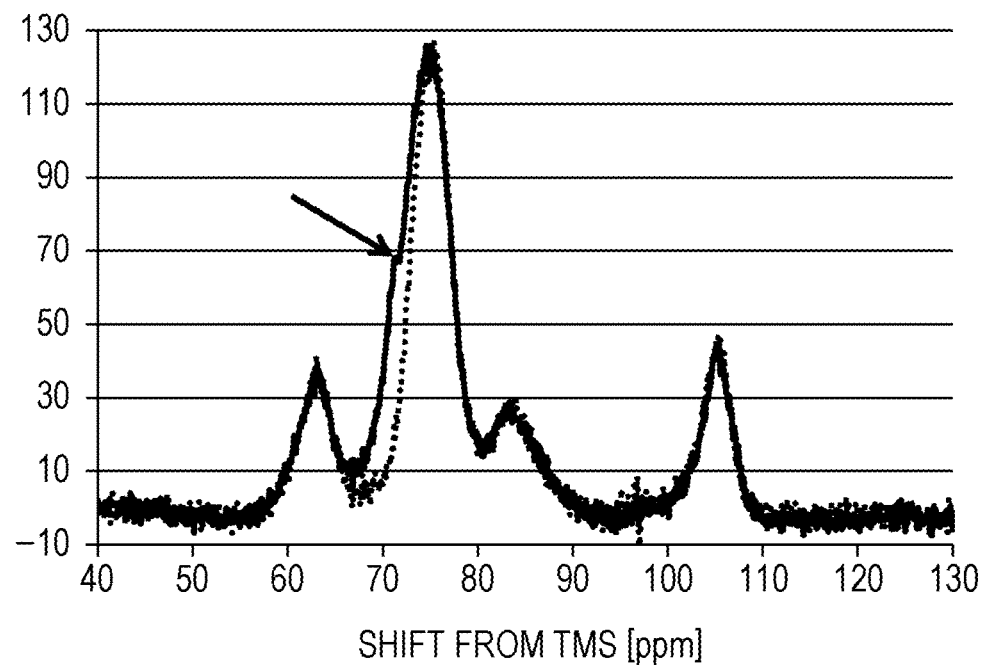
FIG. 1 is a graph that shows an example of a solid state $^{13}$C-NMR spectrum relating to uncrosslinked cellulose and an example of a solid state $^{13}$C-NMR spectrum relating to cellulose crosslinked with PEDE in combination.

The overview of one aspect of the present disclosure is as follows.

Item 1

A polymer having a structure in which cellulose substantially represented by the general formula (I) is crosslinked with a polyfunctional epoxy compound.

Item 2

The polymer according to item 1, wherein the polyfunctional epoxy compound is a diepoxy compound represented by the following general formula (II):

[Chemical Formula 2]

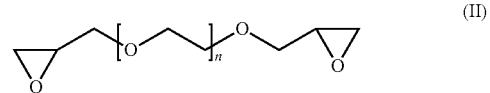

(II)

wherein in the general formula (II), n represents an integer of 1 or more.

Item 3

The polymer according to item 2, wherein the diepoxy compound is one or more kinds of compounds selected from the group consisting of ethylene glycol diglycidyl ether and polyethylene glycol diglycidyl ether.

Item 4

The polymer according to any one of items 1 to 3, wherein β-glucose included in cellulose represented by the general formula (I) has a crosslinked structure on at least one position among 2-position, 3-position and 6-position carbons.

Item 5

The polymer according to any one of items 1 to 4, wherein a crosslinking point carbon ratio calculated based on a peak area included in a spectrum obtained by a solid state $^{13}$C-NMR is equal to or higher than 0.9%.

Item 6

The polymer according to item 5, wherein the crosslinking point carbon ratio is within a range from 9% to 13%, inclusive.

Item 7

A polymer sheet formed of the polymer according to any one of items 1 to 6.

Item 8

The polymer sheet according to item 7, which has a bulk density of higher than 0 g/cm$^3$ and equal to or lower than 0.9 g/cm$^3$.

Item 9

A water absorption body including:

the polymer according to any one of items 1 to 6; and a covering material storing the polymer inside, the covering material being water permeable.

Item 10

A pack for cooling or warming including:

the polymer according to any one of items 1 to 6; and a covering material storing the polymer inside.

Item 11
The polymer sheet according to item 7 or 8, which retains an ingredient that acts on a living body or an ingredient that protects a living body inside a membrane.

Item 12
The polymer sheet according to item 7, 8 or 11 of which at least one part is colored.

Item 13
A laminated sheet including:
the polymer sheet according to item 7, 8, 11 or 12; and
a first protective layer disposed on one principal face of the polymer sheet, the first protective layer is removable from one principal face.

Item 14
The laminated sheet according to item 13, which further includes a second protective layer disposed on the other principal face of the polymer sheet.

Item 15
A method for using a laminated sheet, the method including:
step (a1) of preparing the laminated sheet according to item 13;
step (b1) of causing the other principal face of the polymer sheet to be opposed to the skin;
step (c1) of causing the laminated sheet to be stuck to the skin; and
step (d1) of peeling off a first protective layer from one principal face of the polymer sheet.

Item 16
A method for using a laminated sheet, the method including:
step (a2) of preparing the laminated sheet according to item 14;
step (b2) of peeling off a first protective layer from one principal face of the polymer sheet;
step (c2) of causing one principal face of the polymer sheet to be opposed to the skin;
step (d2) of causing the polymer sheet and the second protective layer to be stuck to the skin; and
step (e2) of peeling off the second protective layer from the other principal face of the polymer sheet.

Item 17
The method according to item 15, further including step (e1) of applying at least one of a liquid and a cream to at least one of the skin and the polymer sheet between step (a1) and step (c1).

Item 18
The method according to item 16, further including step (f2) of applying at least one of a liquid and a cream to at least one of the skin and the polymer sheet between step (a2) and step (d2).

Item 19
The method according to item 17 or 18, wherein the liquid and the cream contains at least one or more selected from the group consisting of water, oil and fat, alcohol and an emulsifying agent.

Item 20
The method according to any one of items 15 to 19, wherein the laminated sheet is used for a cosmetic, medical, protective or decorative sheet.

Item 21
A method for producing a polymer membrane, the method including:
step (A) of preparing a cellulose solution by dissolving cellulose substantially represented by the general formula (I) in a solvent;
step (B) of forming a liquid film on a surface of a base material by applying the cellulose solution on the surface of the base material;
step (C) of crosslinking cellulose in the liquid film with a polyfunctional epoxy compound by applying the polyfunctional epoxy compound on the liquid film while the solvent is caused to be decreased from the liquid film; and
step (D) of removing the solvent included in a crosslinked gel obtained in the step (C).

Item 22
The method according to item 21, wherein the polyfunctional epoxy compound is a diepoxy compound represented by the general formula (II).

Item 23
The method according to item 22, wherein the diepoxy compound is one or more kinds of compounds selected from the group consisting of ethylene glycol diglycidyl ether and polyethylene glycol diglycidyl ether.

Item 24
The method according to any one of items 21 to 23, wherein the step (C) is performed in the presence of a catalyst.

Item 25
The method according to item 24, wherein the catalyst is an alkaline metal hydroxide.

Item 26
The method according to any one of items 21 to 25, wherein cellulose substantially represented by the general formula (I) has a weight-average molecular weight of equal to or higher than 170,000.

Item 27
The method according to any one of items 21 to 26, including step (E) of gelling the liquid film between the step (B) and the step (C).

Item 28
The method according to item 27, wherein the step (E) includes step (E1) of making the liquid film in contact with a vapor of water or an organic polar solvent.

Item 29
The method according to any one of items 21 to 28, wherein the solvent contains at least an ionic liquid.

Item 30
The method according to item 29, wherein the step (A) further includes step (A1) of diluting the cellulose solution.

Item 31
The method according to item 30, wherein the step (A1) is a step performed by diluting the ionic liquid or a mixture of the solvent and the cellulose substantially represented by the general formula (I) with a second solvent.

Item 32
The method according to item 31, wherein the second solvent is an aprotic polar solvent having an SP value of equal to or higher than 12.

Item 33
The method according to item 32, wherein the aprotic polar solvent is dimethyl sulfoxide.

Item 34
The method according to any one of items 29 to 33, wherein the step (D) includes:
step (D1) of removing the ionic liquid included in the crosslinked gel obtained in the step (C) from the crosslinked gel by substituting the ionic liquid with a liquid that is capable of dissolving the ionic liquid but does not dissolve cellulose; and after the step (D1),
step (D2) of removing, from the crosslinked gel, a liquid other than the ionic liquid among liquids included in the crosslinked gel.

Item 35

The method according to item 34, wherein in the step (D2), removing of the liquid other than the ionic liquid is performed by any of vacuum drying, heat drying, reduced pressure drying, freeze drying, supercritical drying or subcritical drying.

Item 36

The method according to any one of items 21 to 35, further including step (F) of separating a membrane remaining on the surface of the base material from the surface, after the step (D).

Item 37

The method according to any one of items 21 to 36, further including step (G) of immersing the membrane obtained in step (F) in a solution containing an ingredient that acts on a living body or an ingredient that protects a living body, and then drying the membrane.

Hereinafter, embodiments of the present disclosure are described in detail with reference to the drawings. Meanwhile, each of embodiments described below shows a comprehensive or specific example. Numerical values, shapes, materials, constituent elements, disposed and connected forms of constituent elements, steps, the order of steps and the like shown in the following embodiments are illustrative, and they do not intend to limit the present disclosure. Various aspects described in the present specification can be combined provided that there are no contradictions. In addition, among constituent elements in the following embodiments, constituent elements that are not described in the independent claim that shows the top concept are described as arbitrary constituent elements. In the following description, a constituent element that has substantially the same function is indicated by a common reference sign, and there are some cases where the description is omitted. Further, in order to suppress excessive complication of the drawings, there are some cases where illustration of some elements is omitted.

Embodiment of Polymer

A polymer according to an embodiment of the present disclosure has a structure in which cellulose is crosslinked with a polyfunctional epoxy compound. The cellulose that constitutes the polymer according to the embodiment of the present disclosure has no chemical modification such as derivatization in a position other than crosslinking points, and is substantially represented by the above-described general formula (I). The phrase that cellulose is "substantially represented by the general formula (I)" means that hydroxy groups equal to or higher than 90% remain in glucose residues in cellulose. The ratio of hydroxy groups of glucose residues in cellulose can be quantified, for example, by known various methods such as X-ray photoelectron spectroscopy (XPS). However, the above-described definition does not intend to exclude that cellulose does not have any branched structure at all. As described later, as materials for forming the polymer according to the embodiment of the present disclosure, both the natural cellulose and regenerated cellulose may be used. Among them, natural cellulose is generally recognized as a linear polymer having no branched structure, but there may be natural cellulose having a branch in the molecular chain. Cellulose to which a branched structure is artificially introduced is not included in cellulose "substantially represented by the general formula (I)". Cellulose having artificial derivatization is not included in cellulose "substantially represented by the general formula (I)", either. However, from cellulose "substantially represented by the general formula (I)", all the regenerated cellulose that has been once subjected to derivatization is not necessarily excluded. There may be cases where regenerated cellulose that has been once subjected to derivatization is encompassed in cellulose "substantially represented by the general formula (I)".

As the polyfunctional epoxy compound, a compound having 2 or more oxirane rings may be used. For example, as the polyfunctional epoxy compound, a diepoxy compound represented by the above-described general formula (II) may be used. The diepoxy compound represented by the general formula (II) has oxirane rings at both ends and easily forms a crosslinked structure by reacting with a hydroxy group included in cellulose. The above-described ethylene glycol diglycidyl ether (EGDE) and polyethylene glycol diglycidyl ether (PEDE) are compounds having the general formula (II) in which n=1 and n≥2, respectively. Examples of the diepoxy compound that may be used other than the above include propylene glycol diglycidyl ether, polypropylene glycol diglycidyl ether, neopentyl glycol diglycidyl ether, glycerol diglycidyl ether, 1,4-butanediol diglycidyl ether and the like. Examples of the polyfunctional epoxy compound that may be used further include a compound having three oxirane rings such as trimethylolpropane triglycidyl ether as well as a compound having 4 or more oxirane rings. As the polyfunctional epoxy compound, each of them may be used singly or two or more kinds of them may be used in combination.

The polymer according to the embodiment of the present disclosure has a crosslinked structure in which at least one position among 2-position, 3-position and 6-position carbon atoms of β-glucose in cellulose represented by the above-described general formula (I). The following formula [Chemical Formula 8] shows one example of the polymer according to the embodiment of the present disclosure.

[Chemical Formula 8]

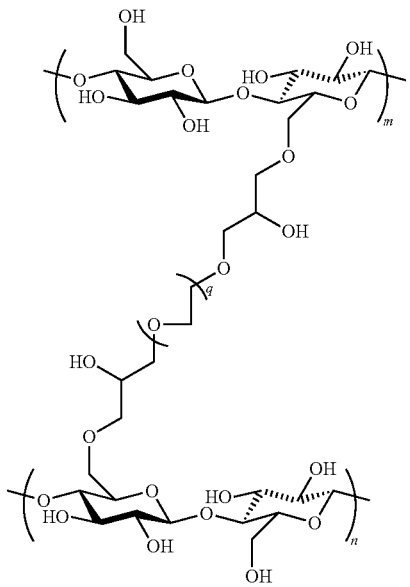

wherein in [Chemical Formula 8], q, m and n each independently represent an integer of 1 or more.

In this example, carbon atoms at 6-position of glucose residues of two molecular chains are crosslinked with each other. Of course, the crosslinking point is not limited to at 6-position carbon atom, but may be at other positions. The positions of the crosslinking points of glucose residues of two molecular chains are not required to be the same, either.

In the present specification, an average number of molecules of a cross-linking reagent (a cross-linking compound, in this case for example, a polyfunctional epoxy compound) bound to 100 glucose residues of cellulose is defined for convenience as "crosslinking point carbon ratio", and there may be some cases where the crosslinking point carbon ratio is expressed as a percentage of a number of crosslinking points per one glucose residue. The crosslinking point carbon ratio of the polymer according to the embodiment of the present disclosure is, for example, equal to or higher than 0.9%. When the crosslinking point carbon ratio is, for example, equal to or higher than 0.9% (the average number of molecules of the cross-linking reagent bound to 100 glucose residues in cellulose is equal to or higher than 0.9), both a high water absorption ratio and a mechanical strength required for self-supporting are compatible. For example, a self-supporting type polymer sheet may be formed. In the present specification, "self-supporting type polymer sheet" is defined as having capability of maintaining a form as a sheet without any support, and means that the sheet can be lifted as a whole without any damage to the sheet and without any support when a part of the sheet is held by using, for example, fingers, tweezers and the like in order to lift the sheet.

According to the embodiment of the present disclosure, a self-supporting type polymer sheet that can be lifted as a whole in both a dry state and a wet state can be formed. When the crosslinking point carbon ratio is equal to or higher than 9%, an effect of stabilizing a swelled form of the polymer while maintaining a relatively high water absorption ratio can be exhibited by increase in crosslinking points. When the crosslinking point carbon ratio is equal to or lower than 13%, the decrease in the water absorption ratio due to excess crosslinking points can be suppressed and is beneficial.

The crosslinking point carbon ratio can be determined based on a peak area included in a spectrum obtained by a solid state NMR method. FIG. 1 shows an example of a solid state $^{13}$C-NMR spectrum relating to uncrosslinked cellulose and an example of a solid state $^{13}$C-NMR spectrum relating to cellulose crosslinked with PEDE in combination. In FIG. 1, the vertical axis represents the signal strength (arbitrary unit) and the horizontal axis represents the chemical shift taking the resonance frequency of the methyl group of tetramethylsilane (TMS) as 0.

In FIG. 1, spectra depicted by a broken line and a solid line are a spectrum relating to uncrosslinked cellulose and a spectrum relating to cellulose crosslinked with PEDE, respectively. From FIG. 1, it can be understood that with regard to both the cellulose before crosslinking and after crosslinking, peaks appear at around 63 ppm, 75 ppm, 83 ppm and 105 ppm. According to NPL 1, the peak at around 63 ppm is derived from 6-position carbon atom in a glucose residue, and the peak at around 75 ppm is derived from 2-position, 3-position and 5-position carbon atoms. The peaks at around 83 ppm and around 105 ppm are derived from 4-position carbon atom and 1-position carbon atom of a glucose residue, respectively.

Here, referring to a spectrum relating to cellulose after crosslinking (solid line), as indicated by the thick arrow in FIG. 1, a peak at around 70 ppm that was not observed in a spectrum relating to cellulose before crosslinking (broken line) appears. According to NPL 2, this peak is attributed to a methylene carbon of PEDE that was used as a cross-linking reagent (in the above-described general formula (II), two carbon atoms in square brackets representing a repeating unit).

Meanwhile, according to NPL 2, a peak derived from methylene carbons in oxirane rings included in the polyfunctional epoxy compound represented by the above-described general formula (II) appears at around 45 ppm, in the case where the polyfunctional epoxy compound is unreacted. In the example shown in FIG. 1, a peak at around 45 ppm does not appear with regard to the crosslinked cellulose, and therefore, it is thought that almost all the PEDE used as the cross-linking reagent is used for intermolecular crosslinking.

Under such a condition, for example, when a diepoxy compound represented by the above-described general formula (II) is used, the crosslinking point carbon ratio CR can be estimated by the following formula (f1).

[Numerical Formula 1]

$$CR(\%) = \left(\frac{B_{2\text{-}6}}{B_1} - \frac{A_{2\text{-}6}}{A_1}\right) \cdot \frac{1}{2n} \cdot 100 \qquad (f1)$$

In formula (f1), n is a number of repeating units of a diepoxy compound represented by the above-described general formula (II). In addition, in formula (f1), $A_{2\text{-}6}$ is the total area of the range including three peaks within a range from equal to or higher than 55 ppm to lower than 95 ppm in the spectrum relating to cellulose before crosslinking, $A_1$ is a peak area derived from 1-position carbon atom in glucose residues within a range from 95 ppm to 115 ppm, inclusive. $B_{2\text{-}6}$ is the total area of the range including four peaks within a range from equal to or higher than 55 ppm to less than 95 ppm in the spectrum relating to cellulose after crosslinking, and $B_1$ is a peak area derived from 1-position carbon atom in glucose residues within a range from 95 ppm to 115 ppm, inclusive.

When as the cross-linking reagent, a polyfunctional epoxy compound having the repeating unit in the above-described general formula (II), that is, a polyfunctional epoxy compound having a similar structure to polyethylene glycol (PEG) as its part is used, the crosslinking point carbon ratio CR can be basically calculated based on the above-described formula (f1). When other polyfunctional epoxy compounds are used, for example, the crosslinking point carbon ratio CR can be defined as follows.

The total area of a range including all the peaks within a range from equal to or higher than 20 ppm to lower than 180 ppm relating to a spectrum of cellulose before crosslinking is taken as $A_{1\text{-}6}$. In addition, the total area of a range including all the peaks within a range from equal to or higher than 20 ppm to lower than 180 ppm relating to a spectrum of cellulose after crosslinking is taken as $B_{tot}$. In that case, the value calculated by the following formula (f2) is defined as the crosslinking point carbon ratio CR.

[Numerical Formula 2]

$$CR(\%) = \left(\frac{B_{tot}}{B_1} - \frac{A_{1\text{-}6}}{A_1}\right) \cdot \frac{1}{r} \cdot 100 \qquad (f2)$$

In formula (f2), r is a number of carbon atoms of which peaks of solid state $^{13}$C-NMR spectrum appear within a range from equal to or higher than 20 ppm to lower than 180 ppm, among the carbon atoms in the structure other than oxirane rings in the polyfunctional epoxy compound. When a diepoxy compound represented by the above-described general formula (II) is used, the repeating unit of the diepoxy compound contains two carbon atoms, when a number of the repeating unit is n, r is represented by r=2n, and formula (f2) is attributed to formula (f1).

Figure 2:
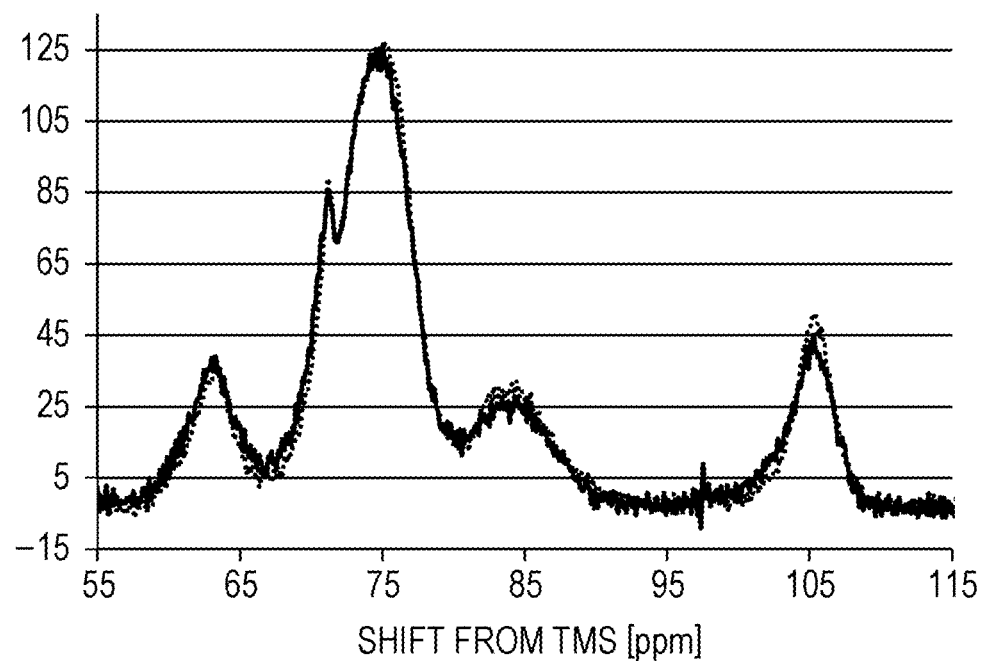
FIG. 2 is a graph that shows other two examples of solid state $^{13}$C-NMR spectra relating to cellulose crosslinked with PEDE in combination.

FIG. 2 shows two other examples of solid state $^{13}$C-NMR spectra relating to cellulose crosslinked with PEDE in combination. In FIG. 2, a spectrum depicted by a broken line is a spectrum relating to a crosslinked cellulose that was produced by cellulose having a weight-average molecular weight of 30,800, and a spectrum depicted by a solid line is a spectrum relating to a crosslinked cellulose that was produced by cellulose having a weight-average molecular weight of 305,000.

As shown in FIG. 2, two spectra relating to crosslinked cellulose having different weight-average molecular weights of cellulose are approximately the same. Accordingly, in order to compare crosslinked celluloses produced from cellulose having different weight-average molecular weights, the crosslinking point carbon ratio CR calculated from the above-described formula (f1) or formula (f2) can be utilized as an amount characterizing a crosslinked cellulose. Meanwhile, here, in formula (f1) and formula (f2), a peak area derived from 1-position carbon atom in glucose residues is used as a normalized factor, a peak area derived from carbon atom at another position in glucose residues may be used for normalization.

As described below with reference to Examples, according to the embodiment of the present disclosure, a polymer sheet composed of the above-described polymer can be formed. The polymer sheet has, for example, a bulk density of higher than 0 g/cm$^3$ and equal to or lower than 0.9 g/cm$^3$. When the bulk density of the polymer sheet is equal to or lower than 0.9 g/cm$^3$, the polymer sheet can absorb a larger amount of water and is beneficial. It is assumed that this makes water enter easily into inside of a crosslinked cellulose because of the increase in a void within the polymer sheet, and as a result, the polymer sheet swells more easily.

In addition, according to the embodiment of the present disclosure, a polymer sheet that is capable of maintaining a sheet form without any support can be provided. The polymer sheet according to the embodiment of the present disclosure, in a dry state, may have tensile strength almost equivalent to a sheet of polycarbonate, triacetate, polyether imide, nylon 6 or the like. The polymer sheet according to the embodiment of the present disclosure is capable of maintaining a form as a sheet without any support even in a wet state, and may have mechanical strengths to a degree at which, for example, tensile testing can be carried out.

Method for Producing Polymer Membrane

Next, an example of a method for producing a polymer membrane according to an embodiment of the present disclosure is described.

Figure 3:
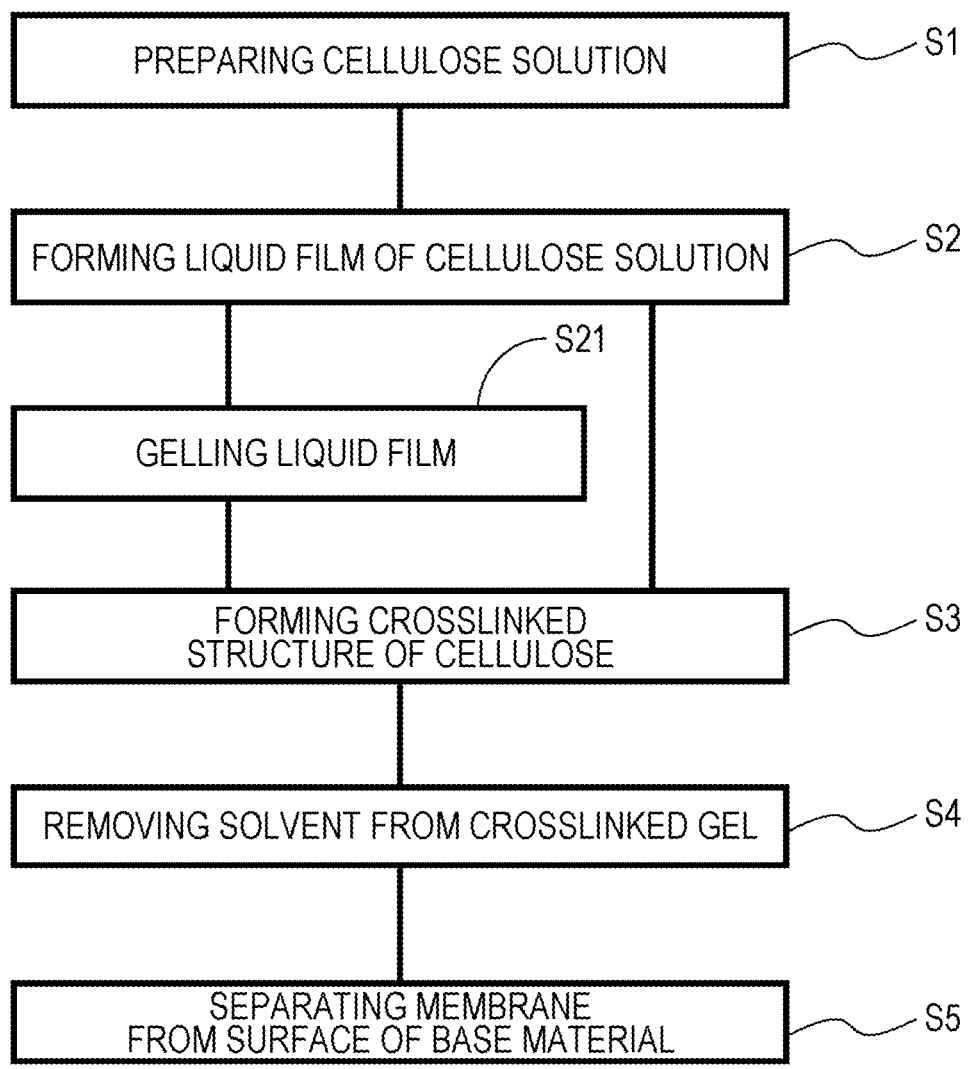
FIG. 3 is a chart that describes an example of a method for producing a polymer membrane according to an embodiment of the present disclosure.

FIG. 3 is a view that illustrates an example of the method for producing the polymer membrane according to the embodiment of the present disclosure. As shown in FIG. 3, an exemplary method for producing a polymer membrane roughly encompasses step of preparing a cellulose solution (step S1), step of forming a liquid film of the cellulose solution (step S2), step of forming a crosslinked structure of cellulose (step S3), and step of removing a solvent included in a crosslinked gel (step S4). Hereinafter, each step is described in details.

First, in step of preparing a cellulose solution (step S1), a cellulose solution is prepared by dissolving cellulose in a solvent. As cellulose to be dissolved in a solvent, cellulose substantially represented by the above-described general formula (I) is used. Cellulose dissolved in a solvent may be natural cellulose or synthetic cellulose. Examples of natural cellulose that may be used include cellulose derived from a plant such as pulp or cotton, alternatively, cellulose produced by an organism such as a bacterium and the like. Synthetic cellulose such as cellophane may be dissolved in a solvent. The form of cellulose is not particularly limited, and for example, commercially available microcrystalline cellulose may be utilized as a raw material.

Examples of the solvent that can be used for dissolving cellulose include an aqueous solution of an acid, an alkali or the like, for example, an organic solvent such as dimethylacetamide to which lithium chloride is added, and the like. Alternatively, examples of the solvent that can be used include an ionic liquid. The ionic liquid is a salt that is liquid in a wide range of temperature, and has been attracting more attention in recent years as a solvent that is capable of dissolving cellulose having a high molecular weight without significantly decreasing a weight-average molecular weight. From the viewpoint of obtaining a sheet of a crosslinked cellulose that is capable of maintaining a form as a sheet even in a water-absorbed state, it is advantageous to use the ionic liquid that is capable of dissolving cellulose having a high molecular weight without significantly decreasing a weight-average molecular weight of cellulose that is used as a raw material.

The ionic liquid is a salt composed of an anion and a cation and is capable of exhibiting a liquid state at a temperature equal to or lower than 150° C. Examples of the ionic liquid that can be used include a pair of a cation (left side) and an anion (right side) represented by the following general formula (III).

[Chemical Formula 9]

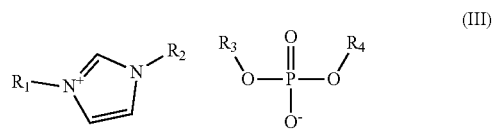

(III)

In the general formula (III), $R_1$, $R_2$, $R_3$ and $R_4$ independently represent a hydrogen atom or an alkyl group having 1 to 4 carbon atoms. For example, $R_1$ is a methyl group, $R_2$ is an ethyl group, and $R_3$ and $R_4$ are a methyl group or an ethyl group.

Of course, the ionic liquid is not limited to this example. The ionic liquid may contain an imidazolium-based cation. Alternatively, as an ionic liquid that dissolves cellulose, an ionic liquid containing an amino acid or an alkyl phosphoric ester may be used. By using such the ionic liquid as a solvent, it is possible to dissolve cellulose while suppressing significant decrease in the molecular weight. In particular, an amino acid is an ingredient that is present in a living body, and therefore, it can be said that an ionic liquid containing an amino acid can make it possible to create a regenerated cellulose membrane that is safer to a living body. For example, an ionic liquid represented by the following general formula (IV) can be used. The ionic liquid represented by the general formula (IV) is an example in which an anion is an amino acid. As apparent from the general formula (IV), in this example, the anion contains the terminal carboxyl group and the terminal amino group. The cation of the ionic liquid represented by the general formula (IV) may be a quaternary ammonium cation.

[Chemical Formula 10]

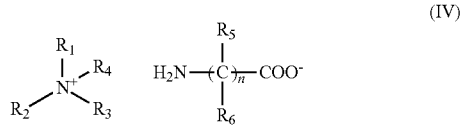

(IV)

In the general formula (IV), $R_1$ to $R_6$ independently represent a hydrogen atom or a substituent. The substituent may be an alkyl group, a hydroxyalkyl group or a phenyl group, and may contain a branch in the carbon chain. The substituent may contain an amino group, a hydroxyl group, a carboxyl group and the like.

Cellulose may be dissolved by using the ionic liquid diluted beforehand with a solvent that does not precipitate cellulose. For example, examples of the solvent that may be used to dissolve cellulose include a mixture of an aprotonic polar solvent and an ionic liquid. A protic solvent tends easily to form hydrogen bonding and may precipitate cellulose. Accordingly, from the viewpoint of diluting a cellulose solution stably, an aprotonic polar solvent is more suited. Examples of the solvent used for dilution include an aprotonic polar solvent having a Solubility Parameter (SP) value of equal to or higher than 12. Here, an SP value is a Hildebrand solubility parameter calculated from molar heat of vaporization according to the regular solution theory. Examples of the aprotonic polar solvent having an SP value of equal to or higher than 12 include dimethyl sulfoxide and the like. By using the ionic liquid diluted beforehand, cellulose can be dissolved in a short period of time. In particular, when a ratio of the ionic liquid in the solvent that dissolves cellulose is equal to or higher than 50 wt %, an effect of improving solubility of cellulose can be exhibited.

In the step of preparing the cellulose solution, the cellulose solution may be diluted. For example, a mixture of cellulose and a first solvent containing at least an ionic liquid may be diluted with a second solvent. Examples of the second solvent that may be used include a solvent that does not precipitate cellulose, and an aprotonic polar solvent having an SP value of equal to or higher than 12 may be used.

A weight-average molecular weight of cellulose dissolved in a solvent is not particularly limited. By using the ionic liquid as the solvent, for example, it may be possible to prepare a cellulose solution in which cellulose having a weight-average molecular weight of equal to or higher than 150,000 (one hundred and fifty thousand) is dissolved. It is especially advantageous when a weight-average molecular weight of cellulose to be dissolved in a solvent is within a range from 170,000 (one hundred and seventy thousand) to 1,700,000 (1.7 million), inclusive (that is n in the above-described general formula (I) is within a range from about 1,050 to about 10,500, inclusive). When a weight-average molecular weight of cellulose dissolved in a solvent is equal to or higher than 170,000, a stable structure can be formed without making a crosslinking density too large. Since it is not required to make a crosslinking density excessively large, larger voids among the molecular chains of cellulose can be formed, and it is possible to provide a polymer sheet that swells more easily. In other words, it is possible to provide a polymer sheet having a high water absorption ratio. When a weight-average molecular weight is equal to or lower than 1,700,000, it is possible to suppress that a viscosity of the cellulose solution becomes excessively high, and therefore, in the next step (step S2), an effect of making it easy to form a liquid film of the cellulose solution can be exhibited. Meanwhile, according to the embodiment of the present disclosure, even when a weight-average molecular weight is relatively high in this manner, it is possible to form crosslinking among cellulose.

In a step for forming a liquid film of the cellulose solution (step S2), a base material is prepared, and the cellulose solution is applied on the surface of the base material such that a liquid film is formed on the surface of the base material. The base material is not particularly limited, and examples of the base material that may be used include a glass plate, a resin plate such as polyethylene terephthalate and polypropylene and the like. In the case when a thin sheet having a thickness of equal to or lower than about 1.3 μm is formed, it is advantageous to apply the cellulose solution on the surface of a base material having a hydrophilic surface. For the formation of the liquid film, for example, gap coating, slot die coating, spin coating, coating that uses a bar coater (Metering rod coating), gravure coating or the like can be applied. The gap coating and the slot die coating are advantageous because, even when the cellulose solution has a high viscosity, a liquid film can be stably formed, and further, the maintenance is easy. By adjusting the size of the opening of the gap or the slot die or the concentration of the cellulose solution, it is possible to adjust the thickness of a finally obtained cellulose membrane. Alternatively, in order to form the liquid film, a casting method, a screen printing method using a squeegee, or, spray painting, electrostatic spraying or the like may be applied.

Step S3 shown in FIG. 3 is a step of forming a crosslinked structure of cellulose by decreasing the solvent (for example, the ionic liquid) from the liquid film while applying a cross-linking compound (here, a polyfunctional epoxy compound) to the liquid film such that the cross-linking compound and cellulose form chemical bonding. By forming the liquid film containing cellulose, and causing cellulose to react with the cross-linking compound (formation of covalent bonding), a sheet-shaped crosslinked cellulose can be formed. Examples of the cross-linking compound that may be used include a polyfunctional epoxy compound such as a diepoxy compound. Two or more kinds of polyfunctional epoxy compounds may be used. For example, by using the above-described EGDE or PEDE, or a mixture of EGDE and PEDE as the cross-linking compound, a water absorptive sheet of the polymer that is hydrophilic and is highly safe to a living body can be formed.

Application of the cross-linking compound to the liquid film can be carried out, for example, by immersing the liquid film in a solution in which the cross-linking compound is dissolved in a solvent. Examples of the solvent that dissolves the cross-linking compound and that may be used include a solvent that is capable of dissolving the ionic liquid and unreacted cross-linking compounds and that does not inhibit the crosslinking reaction. Examples of such the solvent include water, methanol, ethanol, propanol, dimethyl sulfoxide, acetone, dimethylacetamide and the like. From the viewpoint of high safety and low cost, water is advantageous.

In this manner, for example, by using the ionic liquid as the solvent to prepare the cellulose solution, and proceeding the crosslinking reaction by removing the solvent partially from the liquid film of the cellulose solution, a conventionally difficult crosslinked structure of cellulose having a high molecular weight can be formed. The reason is assumed that the solvent that dissolves cellulose (here, the ionic liquid) is substituted with the cross-linking compound, whereby the crosslinking reaction occurs efficiently. For example, by immersing the liquid film in the solution in which the cross-linking compound is dissolved in the solvent, the ionic liquid around a hydroxy group of the molecular chain of cellulose in the liquid film is partially removed, and it is assumed that the crosslinking reaction occurs with higher probability than hydrogen bonding between hydroxy groups. That is, by proceeding the crosslinking reaction while mildly removing the ionic liquid, it is thought to be possible to form more chemical bonds between cellulose and the cross-linking compound.

In the above-described step of forming the crosslinked structure of cellulose (step S3), it is advantageous to use a catalyst, further. Examples of the catalyst that may be used include an alkali metal hydroxide such as potassium hydroxide, sodium hydroxide, and lithium hydroxide in the form of a solution. For example, an aqueous solution of sodium hydroxide is advantageous from the viewpoint of cost reduction. The catalyst may be used by being dissolved in the solution of the cross-linking compound.

As illustrated in FIG. 3, step of gelling the liquid film (step S21) may be performed between step of forming the liquid film of the cellulose solution (step S2) and the above-described step of forming a crosslinked structure of cellulose (step S3). By exposing the liquid film to a vaper of the liquid, that is capable of dissolving the ionic liquid and that does not dissolve cellulose, the liquid film may be gelled. For example, when the liquid film is allowed to stand under an atmosphere of water vapor such that the liquid film is caused to contact with water vapor, the liquid film may be gelled. When the liquid film is allowed to stand under an atmosphere of water vapor, the ionic liquid is mixed with water, whereby the solubility of cellulose decreases, and cellulose molecules aggregate to form a 3-dimensional structure, and finally, it is thought that the liquid film is gelled. Instead of water vapor, for example, a vapor of an organic polar solvent such as methanol, ethanol, propanol, acetone, and dimethylacetamide may be used. The liquid film may be contacted with a mixed vapor of water and one or more kinds of organic polar solvents. Alternatively, the liquid film may be contacted with a mixed vapor of two or more kinds of organic polar solvents.

Step of gelling the liquid film is not an essential step. However, by gelling the liquid film, the water absorption ratio of the crosslinked cellulose may be improved. When the liquid film is contacted, for example, with water vapor, a part of the ionic liquid within the liquid film is removed, and hydrogen bonding among hydroxy groups in the molecular chains of cellulose is partially formed again. When the hydrogen bonding between the molecular chains of cellulose increases, in step of forming a crosslinked structure of cellulose (step S3), it becomes easier for the cross-linking compound to intrude into the inside of the crosslinked gel, whereby it becomes possible to form a crosslinked structure more uniformly. Since more uniform crosslinked structure is formed, even when the crosslinked cellulose swells, it becomes easier to maintain the structure, and as a result, a water absorption ratio may be improved.

On the other hand, according to studies by the present inventors, when immediately after forming the liquid film, the liquid film is immersed, for example, in the aqueous solution in which the cross-linking compound is dissolved, the solvent that dissolves cellulose (here, the ionic liquid) tends to remain inside the membrane, and therefore, it tends to be difficult to form a uniform crosslinked structure. It is assumed that when the liquid film is immersed in the aqueous solution of the cross-linking compound without undergoing step of gelling, the ionic liquid at around the surface of the liquid film is removed preferentially, whereby hydrogen bonding between the molecular chains of cellulose at around the surface of the liquid film increases, and then it becomes difficult for the cross-linking compound to penetrate inside the liquid film, and as a result, a crosslinked structure tends not to be formed uniformly inside the liquid film.

Next, a solvent such as an ionic liquid included in a crosslinked gel obtained by forming a crosslinked structure of cellulose is removed (step S4). In the case where an ionic liquid is used for dissolving cellulose, typically, first, the ionic liquid included in the crosslinked gel is removed, and thereafter, among liquids included in the crosslinked gel, a liquid other than the ionic liquid is removed from the crosslinked gel.

For example, by immersing the crosslinked gel in a liquid, that is capable of dissolving an ionic liquid and that does not dissolve cellulose (hereinafter, sometimes referred to as a "rinse liquid"), it is possible to replace the ionic liquid included in the crosslinked gel with the rinse liquid, and to remove the ionic liquid from the crosslinked gel. Examples of the liquid (rinse liquid) that immerses the crosslinked gel that may be used include a polar solvent that is capable of dissolving an ionic liquid, an unreacted cross-linking reagent and a catalyst and that does not dissolve cellulose. Examples of such the solvent include water, methanol, ethanol, dimethyl sulfoxide and the like. From the viewpoint of safety and low cost, it is advantageous to use water as the rinse liquid. The rinse liquid may be the same as the liquid for gelling the liquid film, but they may be different from each other. However, when a catalyst is used in step of forming the crosslinked structure of cellulose, a polar solvent that is capable of dissolving the catalyst is selected as the rinse liquid. In step of immersing the crosslinked gel in the rinse liquid, a solvent that dissolves a cross-linking compound and/or a catalyst, an unreacted cross-linking reagent, a catalyst and the like may be removed from the crosslinked gel.

Meanwhile, it is possible to perform removal of the ionic liquid before step of forming a crosslinked structure of cellulose (step S3). However, when a large amount of the ionic liquid is removed, for example, from the liquid film before application of the cross-linking compound, hydrogen bonding between hydroxy groups included in the molecular chains of cellulose is formed again, and it tends to be difficult to obtain a high crosslinking density. Accordingly, from the viewpoint of improving the crosslinking density, it is advantageous to perform step of forming a crosslinked structure of cellulose and step of removing a solvent and the like from the crosslinked gel in the order illustrated in FIG. 3.

Next, a liquid other than the ionic liquid is removed from the crosslinked gel. In other words, among a solvent used for diluting the ionic liquid or cellulose solution, a liquid used for gelling the liquid film, a solvent used for dissolving the cross-linking compound, a solvent used for dissolving the catalyst, and the rinse liquid, a part remaining in the crosslinked gel is removed from the crosslinked gel such that a crosslinked gel containing cellulose is dried. Examples of the method for drying that can be applied include various drying methods such as natural drying, vacuum drying, heat drying, reduced pressure drying, freeze drying, supercritical drying and subcritical drying. Vacuum heating may be also performed. Conditions for drying are not particularly limited, and a time period and a temperature sufficient for removing at least the rinse liquid can be applied. By removing the rinse liquid and the like from the crosslinked gel, the polymer membrane according to the embodiment of the present disclosure can be obtained.

In this step, for example, when vacuum drying or heat drying is applied, the polymer membrane having a relatively high bulk density can be obtained. Meanwhile, when for example, freeze drying is applied, the polymer membrane having a lower bulk density as compared to the case where vacuum drying or heat drying is applied tends to be obtained. Hereinafter, a polymer sheet having a bulk density lower than the true density of cellulose of 1.5 g/cm$^3$ is sometimes referred to as "a polymer sheet having a low bulk density".

When freeze drying is applied, a solvent that is freezable and has a boiling point of around 100° C. to around 200° C. may be used. Examples of the solvent include, water, tert-butyl alcohol, acetic acid, 1,1,2,2,3,3,4-heptafluorocyclopentane, dimethyl sulfoxide and the like, and they can be utilized for freeze drying. It is advantageous that when a solvent used for freeze drying is a solvent that is capable of being dissolved in the rinse liquid. However, even when the solvent used for freeze drying is a solvent that cannot be dissolved in the rinse liquid, freeze drying can be carried out by substituting the rinse liquid remaining in the crosslinked gel with a solvent that is capable of being dissolved in the rinse liquid, and then further substituting the solvent with a solvent for freeze drying.

After that, when necessary, the polymer membrane remaining on the surface of the base material is separated from the surface of the base material (step S5). After the rinse liquid and the like are removed from the crosslinked gel, the membrane remaining on the base material is peeled from the base material, whereby a self-supporting type polymer sheet can be obtained.

According to the embodiment of the present disclosure, for example, a crosslinked cellulose sheet that is capable of maintaining a sheet form not only in a dry state but also in a water-absorbed state and that has been conventionally difficult to prepare can be provided. For example, according to the technique described in PTL 2, it is said that etherification is essential for cellulose to be in an amorphous state. Accordingly, mechanical strengths tend to decrease due to derivatization of cellulose. Meanwhile, PTL 2 discloses a method including adding polydiglycidyl ether as a crosslinking reagent to cellulose to which a catalyst has been added so as to proceed crosslinking reaction, and thereafter further adding an etherificating agent. However, by such a technique, it is thought that cellulose is not sufficiently dissolved, and therefore, it has been difficult to achieve a crosslinking density to a degree for being capable of maintaining a form as a sheet even in a water-absorbed state.

On the contrary, an illustrative production method according to the embodiment of the present disclosure, for example, crosslinking is formed by causing a cross-linking compound to react with cellulose dissolved in an ionic liquid (for example, in the presence of a catalyst). In other words, a crosslinked cellulose that shows water absorbency is obtained without derivatization of cellulose. Accordingly, decrease in hydroxy groups associated with derivatization does not occur, and it is possible to react cellulose with a cross-linking compound in an efficient manner. According to the embodiment of the present disclosure, it is possible to proceed crosslinking reaction while maintaining a high molecular weight of cellulose, and it is possible to avoid decrease in mechanical strengths due to derivatization of cellulose. In addition, since derivatization step is not required, it is also advantageous from the viewpoint of simplification of production process and cost reduction. Further, in the obtained crosslinked cellulose, hydroxy groups at other positions than crosslinking points remain, and therefore, the advantage of being capable of conducting chemical modification at the positions of hydroxy groups can be obtained.

Application Example

Figure 4:
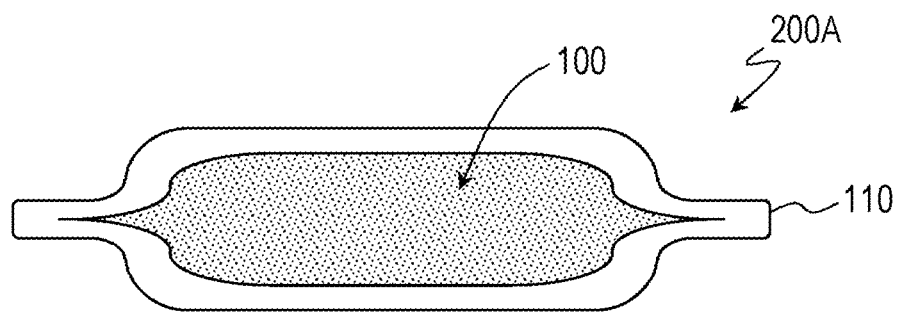
FIG. 4 is a schematic cross section that shows an application example of a polymer according to an embodiment of the present disclosure.

FIG. 4 shows an application example of the polymer according to the embodiment of the present disclosure. FIG. 4 schematically shows a cross section of illustrative water absorption body 200A having polymer 100 inside, that is for example, obtained by the above-described method. Water absorption body 200A shown in FIG. 4 has polymer 100 and covering material 110 that houses polymer 100 inside. Covering material 110 is, for example, formed of a textile fabric such as a non woven fabric, and a dobby, and is composed of water permeable.

Polymer 100 absorbs moisture of the outside of water absorption body 200A via covering material 110. Water absorption body 200A may be used, for example, for a diaper. Another member, for example, a paper that covers polymer 100 may be disposed between covering material 110 and polymer 100. When polymer 100 is retained inside covering material 110, it is not essential that polymer 100 has a form of a sheet, and polymer 100 may take various shapes depending on the shape of covering material 110. Meanwhile, there may be a form that covering material 110 does not cover polymer 100 as a whole, but a part of polymer 100 (for example, one side) is exposed from covering material 110 according to use of water absorption body 200A. Alternatively, a laminated body in which polymer 100 is supported on the principal face of a cloth, a paper, or a resin substrate may be utilized as a water absorption body.

Figure 5:
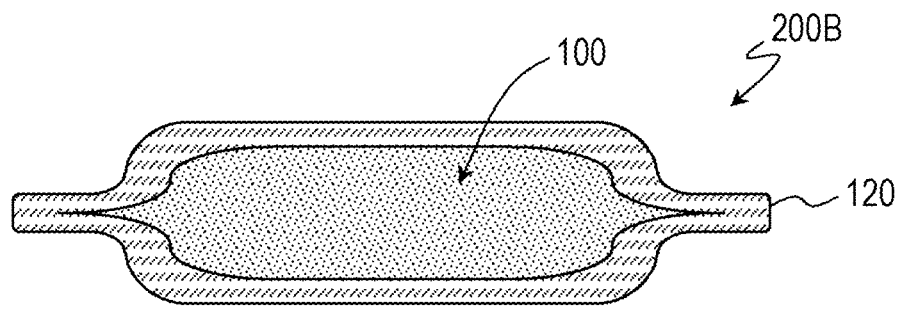
FIG. 5 is a schematic cross section that shows another application example of a polymer according to an embodiment of the present disclosure.

FIG. 5 shows another application example of the polymer according to the embodiment of the present disclosure. FIG. 5 schematically shows a cross section of pack 200B having polymer 100 inside. Pack 200B shown in FIG. 5 has polymer 100 and covering material 120 that houses polymer 100 inside. Covering material 120 is different from covering material 110 shown in FIG. 4 and is basically impermeable. Covering material 120l may be a polyethylene film, a nylon film, or a case of polyethylene and the like.

Polymer 100 housed in covering material 120 is in a state that retains moisture. When pack 200B is cooled, for example, by a freezer or the like, pack 200B can be used as a cooling pack. Alternatively, when pack 200B is heated by using a microwave or the like, pack 200B can be utilized as a warming pack. Meanwhile, needless to say, there are no particular limitations to sizes and shapes of water absorption body 200A described referring to FIG. 4 and those of pack 200B describe referring to FIG. 5.

Figure 6:
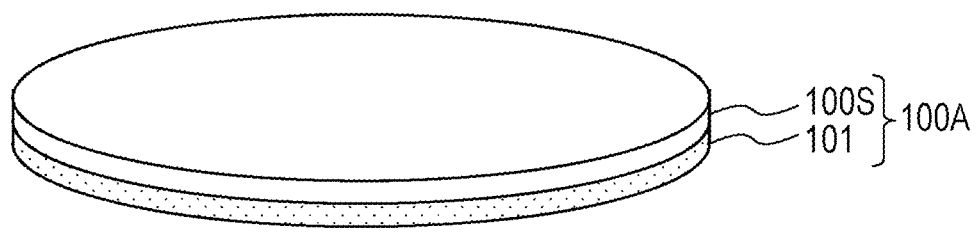
FIG. 6 is a schematic perspective view that show further application example of a polymer according to an embodiment of the present disclosure.
Figure 7:
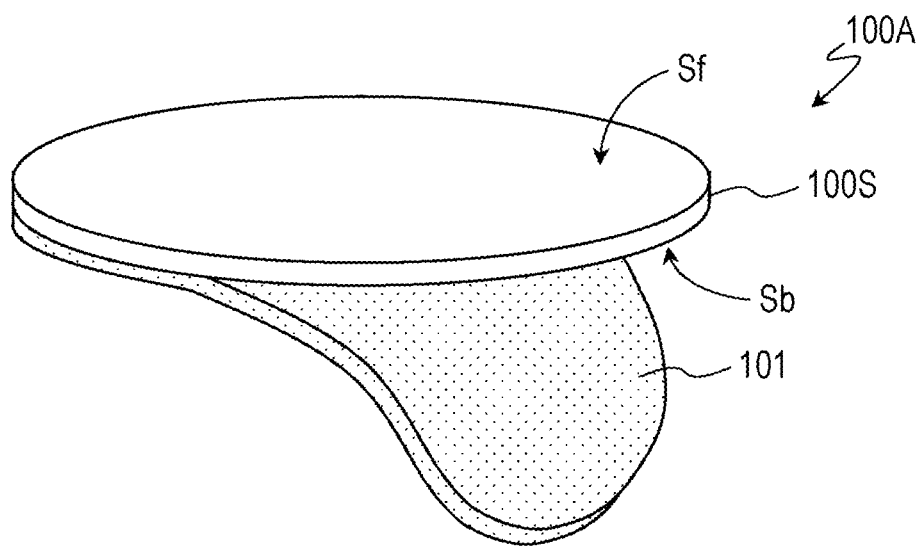
FIG. 7 is a schematic perspective view that shows a state that a part of protective layer 101 is peeled off from one principal face of polymer sheet 100S.

FIGS. 6 and 7 show other application examples of the polymer according to the embodiment of the present disclosure. Polymer sheet 100S shown in FIG. 6 is a sheet formed of the polymer according to the embodiment of the present disclosure.

Polymer sheet 100S may be provided in a form of a laminated body having a protective layer on the principal face of the sheet. Laminated sheet 100A shown in FIG. 6 has polymer sheet 100S and protective layer 101 disposed on one principal face of polymer sheet 100S. Needless to say, FIGS. 6 and 7 just schematically show laminated sheet 100A, and actual sizes are not strictly reflected. In the other drawings of the present disclosure, the polymer sheet and the like may be illustrated in sizes and shapes different from actual sizes and shapes for convenience of explanation.

In this example, polymer sheet 100S has a roughly circular shape. The diameter of polymer sheet 100S shown in FIG. 6 may be, for example, about 3 mm. Of course, the shape of polymer sheet 100S is not limited to the example shown in FIG. 6, but may be elliptic, polygonal or unstructured. In addition, polymer sheet 100S and protective layer 101 may have different sizes. Polymer sheet 100S may have, for example, an area of equal to or higher than 1 $mm^2$. Polymer sheet 100S may have a thickness in a range from about 100 nm to about 10 cm, inclusive.

Referring to FIG. 7, polymer sheet 100S has principal faces Sf and Sb, and here, protective layer 101 is disposed on the side of principal face Sb. Protective layer 101 is, for example, a sheet or a non woven fabric of polyethylene, polypropylene, polyethylene terephthalate, nylon, acrylic resin, polycarbonate, polyvinyl chloride, acrylonitrile-butadiene-styrene (ABS) resin, polyurethane, synthetic rubber, cellulose, Teflon (registered trademark), aramid, polyimide and the like, or, a sheet-shaped metal, glass and the like. In addition, all or part of the surface of the sheet or the non woven fabric may be chemically or physically surface-treated. In this example, protective layer 101 is circular in the same manner as polymer sheet 100S. However, it is not required that polymer sheet 100S and protective layer 101 have the same shape. For example, on single protective layer 101, a plurality of polymer sheets 100S may be disposed. Meanwhile, protective layer 101 in laminated sheet 100A is not a support for maintaining the shape of polymer sheet 100S.

As schematically shown in FIG. 7, protective layer 101 is composed in peelable manner from principal face Sb of polymer sheet 100S. Polymer sheet 100S may have a tensile strength to a degree that is capable of maintaining the shape even in a water absorbing state, in a state where protective layer 101 is peeled off.

Figure 8:
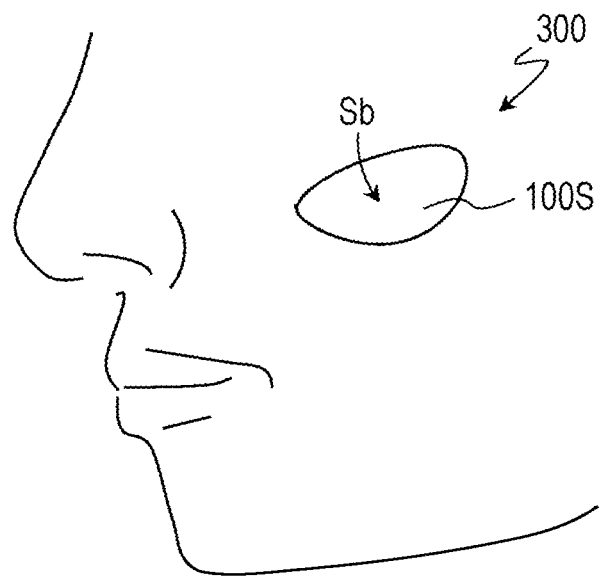
FIG. 8 is a view that shows a use example in which polymer sheet 100S is stuck to a part of a face.

FIG. 8 shows a use example of polymer sheet 100S. FIG. 8 shows a state in which polymer sheet 100S is stuck to skin 300 (here, a part of the skin of a face). As illustrated, polymer sheet 100S may be used by being stuck to a part of a body, for example, a face, an arm and the like.

Here, with reference to FIGS. 9 to 15, an example of a method for using a laminated sheet of the present disclosure is described.

Figure 9:
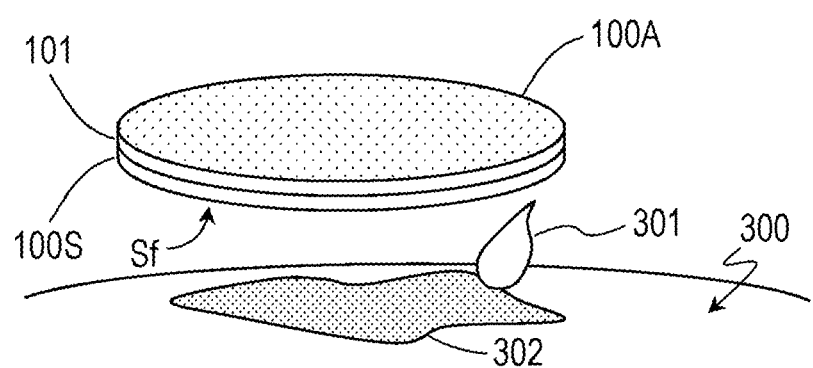
FIG. 9 is a view that illustrates an example in which liquid 301 and/or cream 302 is interposed between polymer sheet 100S and skin 300.

First, the above-described laminated sheet 100A is prepared, and as shown in FIG. 9, among principal faces Sf and Sb of polymer sheet 100S, principal face Sf on which no protective layer 101 is disposed is made to be opposed to a part to which laminated sheet 100A is desired to be stuck. In this example, principal face Sf of polymer sheet 100S is made to be opposed to a part of the skin of a face (skin 300).

At this time, liquid 301 and/or cream 302 such as water may be applied on principal face Sf of polymer sheet 100S or on skin 300. Liquid 301 and cream 302, for example, contain water, oil and fat, alcohol or an emulsifying agent and the like, and may further contain one or more kinds of ingredients for the purposes such as cosmetic or medical application or for the purpose of protecting the skin. For example, cosmetic ingredients such as collagen, hyaluronic acid, various vitamins and derivatives thereof, ceramide, amino acid, placenta, and fullerene may be further contained. Liquid 301 and cream 302 are not limited to cosmetic ingredients, but may contain an ingredient that acts on a living body such as an active ingredient or that protects a living body.

Figure 10:
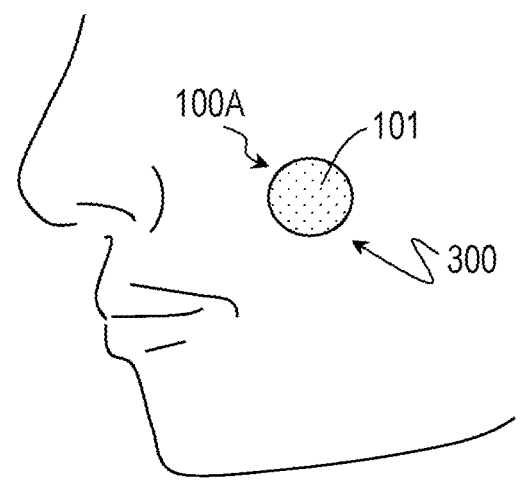
FIG. 10 is a view that shows a state that laminated sheet 100A is stuck to skin 300.
Figure 11:
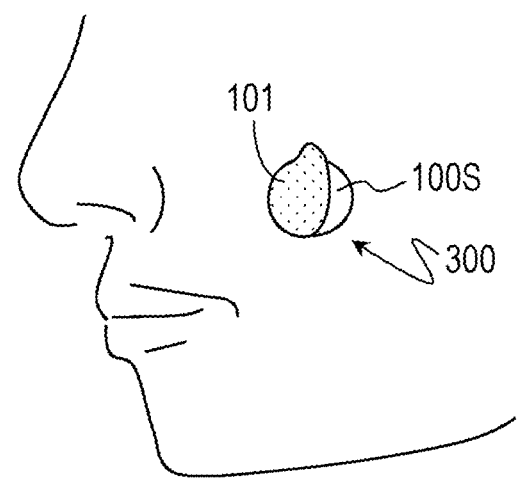
FIG. 11 is a view that shows a state in a course of peeling off protective layer 101 from polymer sheet 100S on skin 300.

Next, as shown in FIG. 10, laminated sheet 100A is stuck to skin 300 by bringing laminated sheet 100A into contact with skin 300 in a state where principal face Sf of polymer sheet 100S is opposed to skin 300. In addition, as shown in FIG. 11, protective layer 101 is peeled off from principal face Sb of polymer sheet 100S. By peeling off protective layer 101 from polymer sheet 100S, it is possible that polymer sheet 100S remains on skin 300 (see FIG. 8).

Figure 12:
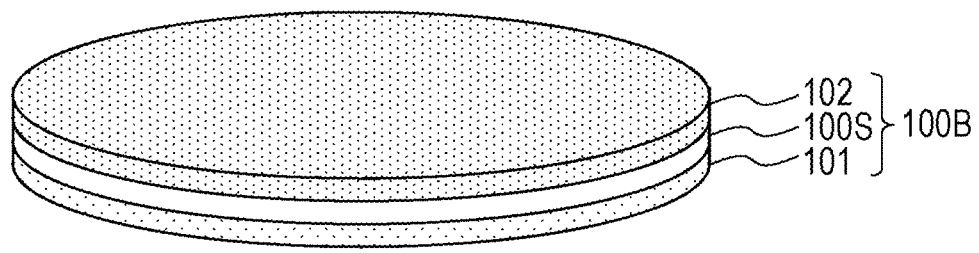
FIG. 12 is a schematic perspective view that shows laminated sheet 100B having polymer sheet 100S, protective layer 101 and second protective layer 102.

On principal face Sf of polymer sheet 100S, another protective layer may be provided. FIG. 12 shows another example of the laminated sheet. Laminated sheet 100B shown in FIG. 12 has second protective layer 102 on a principal face on the opposite side of the principal face on which protective layer 101 is disposed, among principal faces of polymer sheet 100S. Protective layer 102 and protective layer 101 may be composed of the same material or different materials. The size of protective layer 102 may be different from the size of polymer sheet 100S or the size of protective layer 101. Typically, this protective layer 102 is also peelable from polymer sheet 100S in the same manner as protective layer 101. The presence of protective layer 102 makes it easier to handle polymer sheet 100S.

Figure 13:
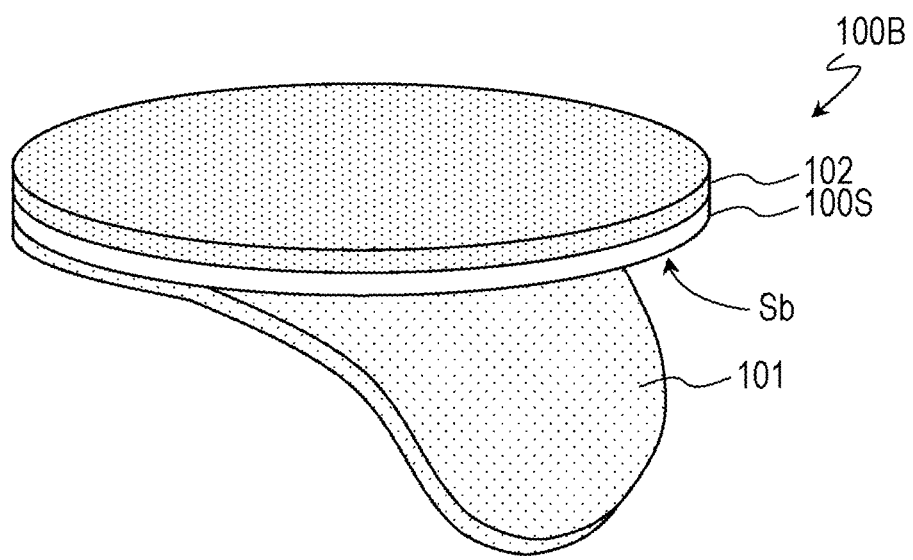
FIG. 13 is a schematic perspective view that shows a state that a part of protective layer 101 is peeled off from polymer sheet 100S of laminated sheet 100B.

When such laminated sheet 100B is used, as shown in FIG. 13, first, protective layer 101 is peeled off from polymer sheet 100S. By removing protective layer 101, principal face Sb of polymer sheet 100S becomes exposed. Thereafter, exposed principal face Sb is made to be opposed to skin 300. In the same manner as in the case of laminated sheet 100A, at that time, liquid 301 and/or cream 302 such as water or skin lotion may be applied on principal face Sb of polymer sheet 100S or on skin 300.

Figure 14:
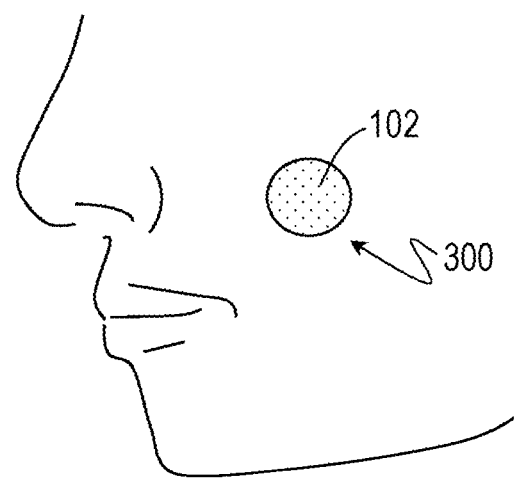
FIG. 14 is a view that shows a state that a laminated body of polymer sheet 100S and second protective layer 102 is stuck to skin 300.

Next, as shown in FIG. 14, a laminated body of polymer sheet 100S and second protective layer 102 is stuck to skin 300. Thereafter, from the other principal face of polymer sheet 100S (the principal face opposite to principal face Sb), protective layer 102 is peeled off. By peeling off protective layer 102, it becomes possible to leave polymer sheet 100S on skin 300.

Figure 15:
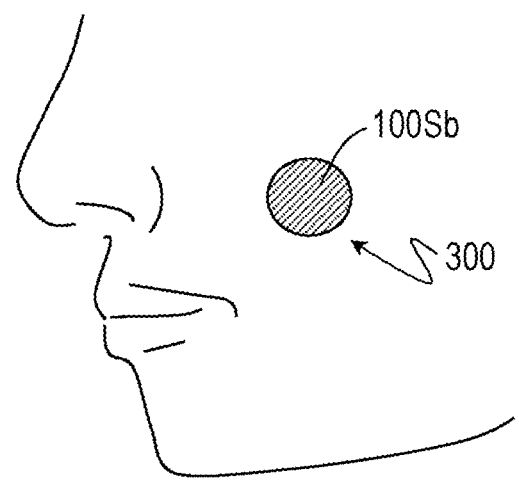
FIG. 15 is a view that schematically shows a state that colored polymer sheet 100Sb is stuck to skin 300.

At least a part of polymer sheet 100S of the present disclosure may be colored. FIG. 15 schematically shows a state in which colored polymer sheet 100Sb is stuck to skin 300. According to the above-described illustrative production method, for example, a transparent or white polymer sheet can be obtained. By using polymer sheet 100Sb colored with a color close to the skin color, a stain, a mole, a scar or the like on skin 300 can be covered with polymer sheet 100Sb, and it is possible to make the stain, the mole, the scar or the like inconspicuous. For example, polymer sheet 100S stuck on a scar can function as a protective sheet that protects the skin from external stimuli. Polymer sheet 100S may retain an ingredient for the medical purpose. Alternatively, when a pattern or a color is applied to the polymer sheet by printing or the like, the polymer sheet may be also utilized as a decorative sheet such as a tattoo seal. Since cellulose is compatible with a living body, and even when cellulose is directly stuck to the skin, the physical or chemical stresses to the skin tend not to be applied. In addition, since cellulose has amphipathic and hydrophilic properties while being incapable of being dissolved in water, it is not necessary to worry about being dissolved in moisture such as sweat, and therefore, cellulose is excellent in durability.

Meanwhile, an ingredient that acts on a living body or that protects a living body such as a cosmetic ingredient or an active ingredient may be retained by the polymer sheet itself. For example, such the ingredients may be retained in voids in the polymer sheet. In particular, when the polymer sheet has a bulk density lower that 1.5 g/cm³, which is the true density of cellulose, a cosmetic ingredient and the like are easier to permeate into the sheet. The ingredient that acts on a living body or that protects a living body such as a cosmetic ingredient may be retained in voids in the sheet in the solid form, or may be retained in voids in the sheet in the form of a solution, a dispersion or a cream by being dissolved and/or dispersed in a liquid. By reducing a bulk density, the polymer sheet that is capable of retaining more moisture and/or a useful ingredient such as a cosmetic ingredient can be provided.

Figure 16:
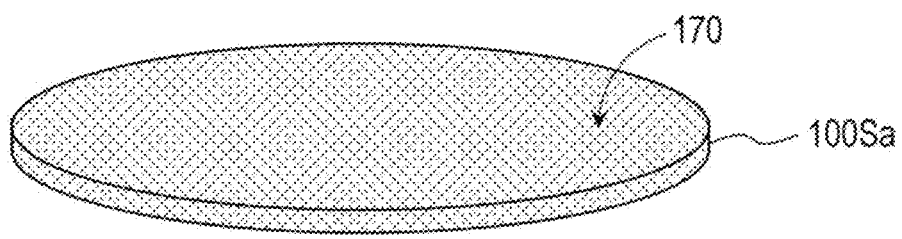
FIG. 16 is a schematic perspective view that shows an example of a polymer sheet that retains an ingredient that acts on a living body or protects a living body.

FIG. 16 shows an example of the polymer sheet that retains an ingredient that acts on a living body or that protects a living body. FIG. 16 shows polymer sheet 100Sa having a roughly circular shape. This is just illustrative, and the shape of polymer sheet 100Sa is not limited to the example shown in FIG. 16.

Polymer sheet 100Sa retains, for example, inside the sheet, cosmetic ingredient 170 as an ingredient that acts on a living body or that protects a living body. The cosmetic ingredient may be present on the surface of the sheet. Whether the polymer sheet retains a useful ingredient such as a cosmetic ingredient can be confirmed, for example, by infrared spectroscopy. Since cellulose is hydrophilic, the polymer sheet according to the embodiment of the present disclosure may be caused to retain a water-soluble ingredient. In addition, since cellulose molecule has amphipathic properties, that is, has a hydrophobic property in addition to a hydrophilic property in combination, it is also possible that the polymer sheet is caused to retain an ingredient having a hydrophobic property. Examples of the water-soluble cosmetic ingredient include hyaluronic acid, vitamin B, vitamin C and derivatives thereof, collagen, placenta and the like, and examples of the cosmetic ingredient having hydrophobic properties include vitamin A, vitamin E, ceramide, fullerene and the like. The polymer sheet is also capable of retaining, a medicinal ingredient inside the sheet as an ingredient that acts on a living body or that protects a living body. Examples of the medicinal ingredient include tacrolimus, isosorbide dinitrate, finasteride, minoxidil and the like. In addition, the polymer sheet may retain an ingredient that protects the skin such as a sunscreening agent. The sunscreening agent includes a material that absorbs ultraviolet rays such as dioxybenzone, and 4-methoxycinnamic acid 2-ethylhexyl ester as well as a material that scatters ultraviolet rays such as titanium oxide, and zinc oxide.

The polymer sheet that retains a cosmetic ingredient and the like can be prepared by obtaining a polymer sheet in accordance with the above-described steps, and thereafter, immersing the polymer sheet in a solution that contains an ingredient that acts on a living body or that protects a living body such as a cosmetic ingredient, taking the polymer sheet out from the solution and drying the polymer sheet. The polymer sheet that retains a useful ingredient such as a cosmetic ingredient can be provided in the form, for example, that a liquid that contains a useful ingredient and the like and the polymer sheet immersed in the liquid are sealed in a package. Alternatively, the polymer sheet that retains a useful ingredient such as a cosmetic ingredient may be provided in the form of a kit that contains, in combination, a dry state polymer sheet, a bottle (or a sachet) that includes a liquid containing a useful ingredient and a tray that receives the liquid discharged from the bottle and that has a recess having a size that is capable of immersing the polymer sheet in the liquid.

EXAMPLES

Hereinafter, the polymer according to the embodiment of the present disclosure is described in detail by referring to Examples. Of course, embodiments of the present disclosure are not limited to the form specified in the following Examples.

Evaluation of Water Absorption Ratio

Example E1-1

First, a bleached pulp of which cellulose has a purity of equal to or higher than 99% and obtained from wood as a raw material was prepared. The weight-average molecular weight of cellulose included in the bleached pulp was measured by a GPC (Gel Permeation Chromatography)-MALS (Multi Angle Light Scattering) method, and the weight-average molecular weight was about 305,000.

In the measurement of a weight-average molecular weight, a liquid transfer unit LC-20AD manufactured by Shimadzu Corporation was used, and as detectors, a differential refractometer Optilab rEX and a multi-angle light scattering detector DAWN HELEOS manufactured by Wyatt Technology Corporation were used. As a column, TSKgel α-M manufactured by TOSOH CORPORATION was used, and as a solvent, dimethylacetamide (DMAC) to which 0.1 M lithium chloride was added was used. The measurement was performed on soluble parts under condition of a column temperature: 23° C., and flow rate: 0.8 mL/min. Meanwhile, between a weight-average molecular weight Mw and n in the above-described general formula (I) (average degree of polymerization), the relation according to the following formula (f3) is established.

[Numerical Formula 3]

$$n = \frac{(Mw - 18)}{162} \tag{f3}$$

The above-described bleached pulp was dissolved in an ionic liquid having the above-described general formula (III) in which $R_2$ is a methyl group, $R_1$, $R_3$ and $R_4$ are an ethyl group to prepare a cellulose solution.

Next, the cellulose solution corresponding to 2.8 mmol in terms of the monomer of the glucose residue was applied on a glass substrate to form a liquid film on the surface of the substrate. In addition, the substrate and the liquid film were allowed to stand under an environment at a temperature of 25° C., and an RH of 30% to 60% for equal to or longer than 6 hours to turn the liquid film into gel.

Thereafter, a reaction solution in which 7.5 mg (0.043 mmol) of EGDE corresponding to the amount of substance of 0.016 times the amount of substance of cellulose in terms of the glucose residue (here, 2.8 mmol) was dissolved in an aqueous solution of 100 mM sodium hydroxide was prepared. The gelled liquid film was immersed in the reaction solution as the substrate as a whole, and cellulose was caused to react with EGDE for 3 hours in a state that the temperature was kept at 60° C. by a hot water bath.

Next, the substrate and a crosslinked gel formed on the substrate were taken out from the reaction solution, and the crosslinked gel on the substrate was washed by immersing in ultrapure water. The crosslinked gel after being washed was subjected to vacuum drying while heating to 70° C. (0.02 MPa, equal to or longer than 2 hours). After that, a membrane remaining on the substrate was peeled off to give a crosslinked cellulose sheet of Example E1-1.

Figure 17:
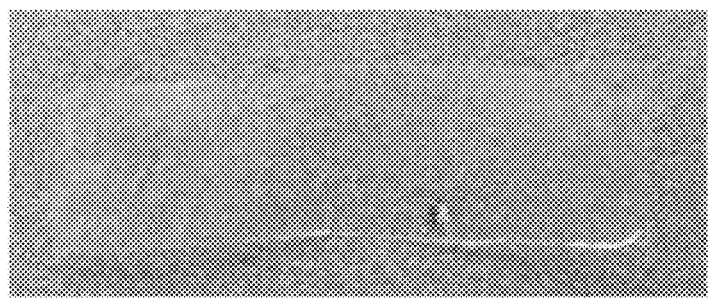
FIG. 17 is a view that represents a photograph showing appearance of a crosslinked cellulose sheet according to Example E1-1.

FIG. 17 shows the appearance of the obtained crosslinked cellulose sheet. As shown in FIG. 17, the crosslinked cellulose sheet of Example E1-1 had a transparent appearance. The crosslinked cellulose sheet of Example E1-1 was placed on a glass substrate, the thickness d of the crosslinked cellulose sheet of Example E1-1 was measured by a Digimatic Indicator manufactured by Mitutoyo Corporation, and the thick ness d was 12 μm. In addition, according to the following procedure, a bulk density $d_B$ of the crosslinked cellulose sheet of Example E1-1 was obtained. First, the crosslinked cellulose sheet was cut out into about 1.5 centimeters square to prepare a sheet piece. The mass W of the sheet piece was measured. Then, an area $A_p$ of the sheet piece projected on a plane was obtained. Then, a bulk density $d_B$ was calculated according to the following formula (f4). A bulk density $d_B$ relating to the crosslinked cellulose sheet of Example E1-1 was 1.5 g/cm³.

[Numerical Formula 4]

$$d_B = \frac{W}{A_p d} \quad (f4)$$

In addition, a crosslinking point carbon ratio CR was calculated according to the above-described formula (f1) by utilizing a solid state $^{13}$C-NMR. In the measurement of $^{13}$C-NMR, Unity Inova-400 manufactured by Varian Medical Systems and a 5 mm CP/MAS probe manufactured by Doty Scientific, Inc. were used, and a CP/MAS method was employed. The measurement conditions were as follows. MAS speed: 10 kHz, room temperature (25° C.), sample spinning speed: 10 kHz, observed width: 30.2 kHz, observation center: 96 ppm, observation frequency: 100.574 MHz. A CP pulse ($^1$H→$^{13}$C) method was employed with following conditions, observation angle 90° pulse: 3.9 μsec, $^1$H excitation pulse: 3.8 μsec, contact time: 2.0 msec, waiting time: equal to or longer than 10 sec, cumulative number: 8,000 times. Meanwhile, the solid state $^{13}$C-NMR spectrum of cellulose measured under these conditions by a CP method was confirmed to be in good agreement with the solid state $^{13}$C-NMR spectrum measured by a DD (Dipolar Decouple) method in which relaxation time was set to be sufficient. The crosslinking point carbon ratio CR obtained by the measurement was 0.58%.

Example E1-2 to Example E1-6

A crosslinked cellulose sheet of each of Example E1-2 to Example E1-7 was prepared in the same manner as Example E1-1 except that the ratio of the amount of substance of EGDE to the amount of substance of cellulose in terms of the glucose residue was changed. Table 1 below shows the ratio of the amount of substance of EGDE to the amount of substance of cellulose in terms of the glucose residue, the crosslinking point carbon ratio CR obtained in the same manner as the sample of Example E1-1, the thickness d and the bulk density $d_B$ of the crosslinked cellulose sheet, relating to each sample of Example E1-1 to Example E1-7 in combination.

TABLE 1

| Sample | Ratio of amount of substance of EGDE to amount of substance in terms of glucose residue | Crosslinking point carbon ratio CR (%) | Thickness d (μm) | Bulk density $d_B$ (g/cm³) |
|---|---|---|---|---|
| Example E1-1 | 0.016 | 0.58 | 12 | 1.5 |
| Example E1-2 | 0.078 | 1.49 | 16 | 1.5 |
| Example E1-3 | 1.6 | 8.72 | 15 | 1.5 |
| Example E1-4 | 3.1 | 11.85 | 14 | 1.5 |
| Example E1-5 | 6.2 | 17.41 | 13 | 1.5 |
| Example E1-6 | 9.3 | 19.78 | 15 | 1.5 |
| Example E1-7 | 15.5 | 24.21 | 12 | 1.5 |

Example P1-1

A crosslinked cellulose sheet of Example P1-1 was prepared in the same manner as Example E1-1 except that the reaction solution was prepared by using 1.5 g (3.0 mmol) of PEDE corresponding to the amount of substance 1.1 times the amount of substance of cellulose in terms of the glucose residue instead of EGDE. Meanwhile, the weight-average molecular weight of PEDE measured by a GPC-MALS method was 500, and therefore, the cross-linking reagent used here was PEDE of which n in the above-described general formula (II) was about 9. Meanwhile, hereinbelow, the ratio of the amount of substance of EGDE to the amount of substance of cellulose in terms of the glucose residue and the ratio of the amount of substance of PEDE to the amount of substance of cellulose in terms of the glucose residue are referred merely to as the "ratio of amounts of substances".

The crosslinking point carbon ratio CR was obtained in the same manner as the sample of Example E1-1, and the crosslinking point carbon ratio CR was 0.88%. In addition, the thickness d and the bulk density $d_B$ of the obtained crosslinked cellulose sheet were 15 μm and 1.5 g/cm³, respectively.

Example P1-2 to Example P1-9

A crosslinked cellulose sheet of each of Example P1-2 to Example P1-9 was prepared in the same manner as Example P1-1 except that the ratio of amounts of substances was changed. Table 2 below shows the ratio of amounts of substances, the crosslinking point carbon ratio CR, the thickness d and the bulk density $d_B$ of the crosslinked cellulose sheet obtained in the same manner as the sample of Example E1-1 relating to each sample of Example P1-1 to Example P1-9 in combination

TABLE 2

| Sample | Ratio of amount of substance of PEDE to amount of substance in terms of glucose residue | Crosslinking point carbon ratio CR (%) | Thickness d (μm) | Bulk density $d_B$ (g/cm$^3$) |
|---|---|---|---|---|
| Example P1-1 | 1.1 | 0.88 | 15 | 1.5 |
| Example P1-2 | 2.2 | 2.63 | 14 | 1.5 |
| Example P1-3 | 5.4 | 5.47 | 13 | 1.5 |
| Example P1-4 | 10.8 | 8.81 | 17 | 1.5 |
| Example P1-5 | 13.5 | 9.73 | 15 | 1.5 |
| Example P1-6 | 16.2 | 11.74 | 16 | 1.5 |
| Example P1-7 | 18.9 | 13.72 | 15 | 1.5 |
| Example P1-8 | 21.6 | 14.33 | 16 | 1.5 |
| Example P1-9 | 27.0 | 17.74 | 15 | 1.5 |

Figure 18:
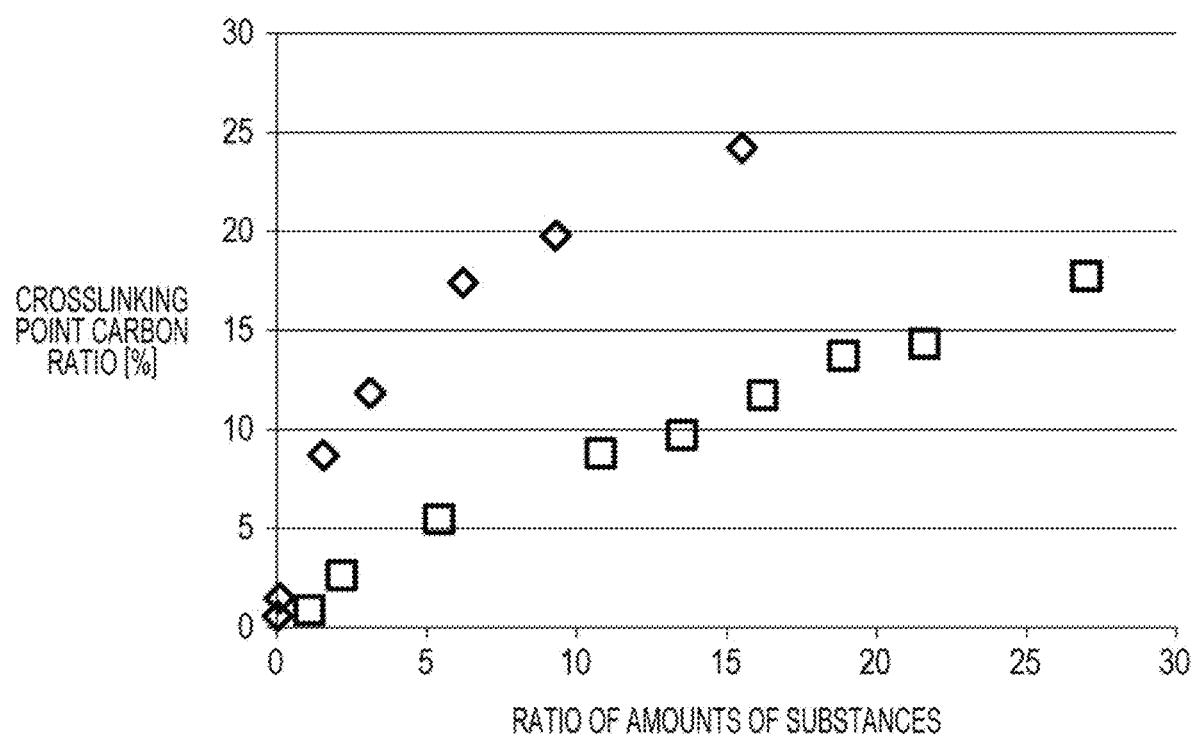
FIG. 18 is a graph that shows relationship between ratios of amounts of substances and crosslinking point carbon ratios with regard to Example E1-1 to Example E1-7 and Example P1-1 to Example P1-9.

FIG. 18 is a graph showing the relationship between the ratios of amounts of substances and the crosslinking point carbon ratios with regard to Example E1-1 to Example E1-7 and Example P1-1 to Example P1-9. In FIG. 18, a white diamond "◇" is a plot relating to each of Example E1-1 to Example E1-7 in which EGDE was used as the cross-linking reagent, and a white square "□" is a plot relating to Example P1-1 to Example P1-9 in which PEDE was used as the cross-linking reagent. From FIG. 18, it can be understood that both the cases where EGDE was used as the cross-linking reagent and PEDE was used as the cross-linking reagent show increase in the crosslinking point carbon ratio when the ratio of amounts of substances increases.

Comparative Example C1-1

Figure 19:
FIG. 19 is a view that represents a photograph showing one example of appearance of a cellulose sheet in which no crosslinking is formed with a cross-linking reagent.

A cellulose sheet of Comparative Example C1-1 was prepared in the same manner as Example E1-1 except that formation of the crosslinked structure by using EGDE was not performed. FIG. 19 shows the appearance of the cellulose sheet of Comparative Example C1-1. The thickness d and the bulk density $d_B$ measured in the same manner as Example E1-1 were 15 μm and 1.5 g/cm$^3$, respectively.

Figure 20:
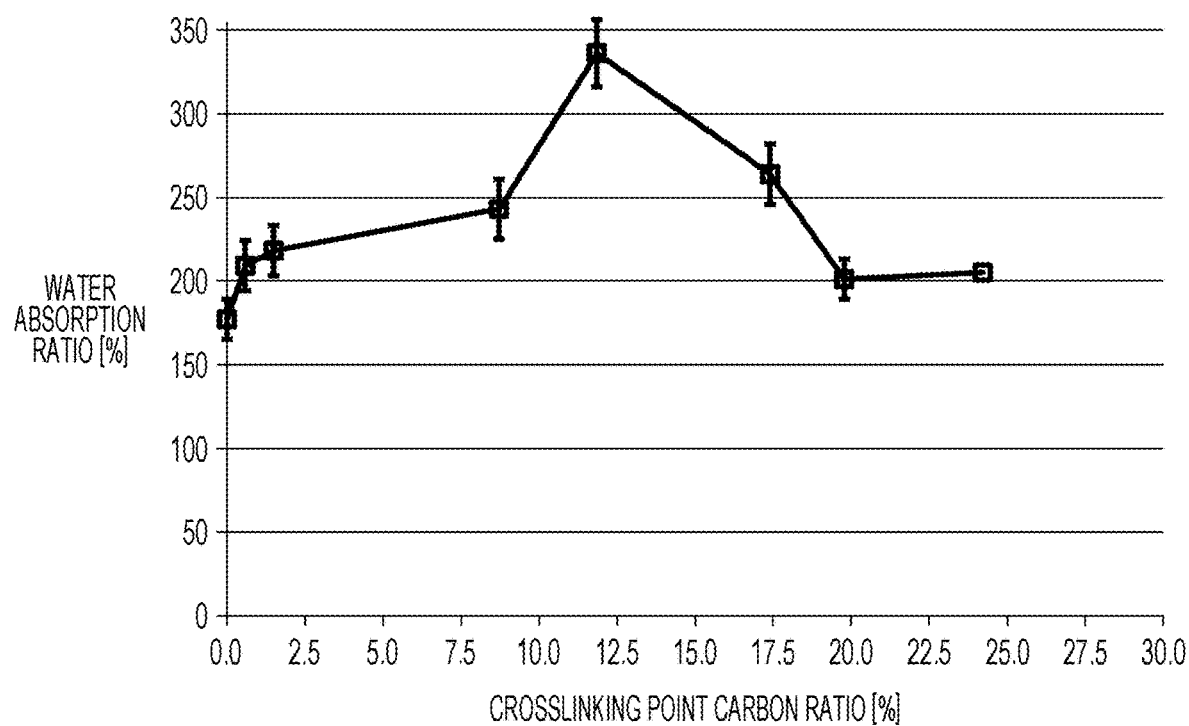
FIG. 20 is a graph that shows relationship between crosslinking point carbon ratios and water absorption ratios relating to Example E1-1 to Example E1-7 and Comparative Example C1-1.

FIG. 20 is a graph showing the relationship between the crosslinking point carbon ratios and the water absorption ratios relating to Example E1-1 to Example E1-7 and Comparative Example C1-1. Meanwhile, each of plots of water absorption ratios shown in FIG. 20 is the mean value of five cellulose sheets.

The measurement of a water absorption ratio of a cellulose sheet can be performed in accordance with a method A of JIS K7209: 2000 6.2. Here, according to the following procedure, a water absorption ratio of a cellulose sheet was determined. First, a sheet that is an object to be measured is dried in an environment of 90° C., and 0.02 MPa for 2 hours. Thereafter, the dry mass M1 of the sheet is measured. Next, the sheet that is the object to be measured is immersed in ultrapure water at a temperature of 23° C. for 24 hours. After that, the sheet is taken out from ultrapure water, and immediately after wiping excess water droplets on the surface, the mass M2 of the sheet is measured. The $A_w$ (%) defined by the following formula (f5) is obtained as the water absorption ratio.

[Numerical Formula 5]

$$A_w = \frac{(M_2 - M_1)}{M_1} \cdot 100 \quad (f5)$$

From FIG. 20, it can be understood that when the crosslinking point carbon ratio is equal to or higher than about 0.58% (the ratio of amounts of substances can be said to be equal to or higher than about 0.016), a crosslinked cellulose sheet having a higher water absorption ratio as compared with the cellulose sheet in which no crosslinked structure is formed by a cross-linking reagent (Comparative Example C1-1) can be obtained. It can be understood with reference to FIG. 20 that when the crosslinking point carbon ratio is 11.9% (at this time, the ratio of amounts of substances is 3.1), the maximum water absorption ratio is exhibited, and when the crosslinking point carbon ratio is within a range from about 8.7% to about 19.8%, inclusive, an especially high water absorption ratio can be obtained. In other words, when the ratio of amounts of substances is within a range from about 1.6 to about 9.3, inclusive, an especially high water absorption ratio can be obtained.

Figure 21:
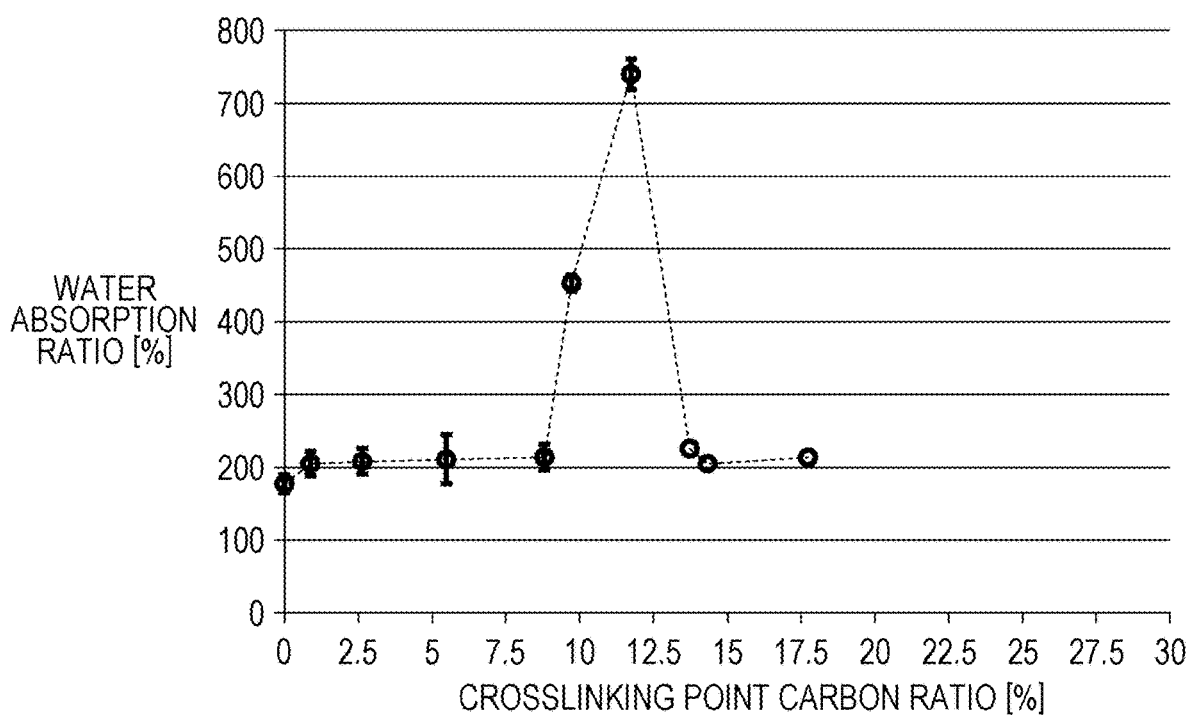
FIG. 21 is a graph that shows relationship between crosslinking point carbon ratios and water absorption ratios relating to Example P1-1 to Example P1-9 and Comparative Example C1-1.

FIG. 21 is a graph showing the relationship between crosslinking point carbon ratios and water absorption ratios relating to Example P1-1 to Example P1-9 and Comparative Example C1-1. Meanwhile, each of plots of water absorption ratios shown in FIG. 21 is the mean value of five cellulose sheets.

From FIG. 21, it can be understood that when the crosslinking point carbon ratio is equal to or higher than about 0.88% (the ratio of amounts of substances can be said to be equal to or higher than about 1.1), a crosslinked cellulose sheet having a higher water absorption ratio as compared with a cellulose sheet having no crosslinked structure (Comparative Example C1-1) can be obtained. It can be understood with reference to FIG. 21 that when the crosslinking point carbon ratio is 11.7% (at this time, the ratio of amounts of substances is 16.2), the maximum water absorption ratio is exhibited and when the crosslinking point carbon ratio is within a range from about 8.8% to about 13.7%, inclusive, an especially high water absorption ratio can be obtained. In other words, when the ratio of amounts of substances is within a range from about 10.8 to about 18.9, inclusive, an especially high water absorption ratio can be obtained.

Example E2 to Example E4

A crosslinked cellulose sheet of each of Example E2 to Example E4 was prepared in the same manner as Example E1-4 (the ratio of amounts of substances: 3.1, crosslinking point carbon ratio: 11.9%) except that cellulose having a different weight-average molecular weight was used to prepare a cellulose solution. As raw materials of cellulose for being dissolved in an ionic liquid, filter paper, cellophane and microcrystalline cellulose (Avicel, "Avicel" is a registered trademark of FMC Corporation) were used. The weight-average molecular weights Mw of cellulose measured by a GPC-MALS method were 170,000, 105,000 and 30,800, respectively.

Comparative Example C2 to Comparative Example C4

A cellulose sheet of each of Comparative Example C2 to Comparative Example C4 was prepared in the same manner as each of Example E2 to Example E4, respectively except that the formation of a crosslinked structure by using EGDE was not performed.

Table 3 below shows weight-average molecular weights of cellulose used as raw materials, the thicknesses d and the bulk densities $d_B$ of cellulose sheets obtained in the same manner as the sample of Example E1-1 relating to each sample of Example E2 to Example E4 and Comparative Example C2 to Comparative Example C4 in combination.

TABLE 3

| Sample | Weight-average molecular weight | Thickness d (μm) | Bulk density $d_B$ (g/cm³) |
|---|---|---|---|
| Example E2 | 170,000 | 17 | 1.5 |
| Example E3 | 105,000 | 14 | 1.5 |
| Example E4 | 30,800 | 17 | 1.5 |
| Comparative Example C2 | 170,000 | 17 | 1.5 |
| Comparative Example C3 | 105,000 | 16 | 1.5 |
| Comparative Example C4 | 30,800 | 14 | 1.5 |

Example P2 to Example P4

A crosslinked cellulose sheet of each of Example P2 to Example P4 was prepared in the same manner as Example P1-6 (the ratio of amounts of substances: 16.2, crosslinking point carbon ratio: 11.7%) except that cellulose having a different weight-average molecular weight was used to prepare a cellulose solution.

Table 4 below shows weight-average molecular weights of cellulose used as raw materials, the thicknesses d and the bulk densities $d_B$ of cellulose sheets obtained in the same manner as the sample of Example E1-1 relating to each sample of Example P2 to Example P4 in combination.

TABLE 4

| Sample | Weight-average molecular weight | Thickness d (μm) | Bulk density $d_B$ (g/cm³) |
|---|---|---|---|
| Example P2 | 170,000 | 15 | 1.5 |
| Example P3 | 105,000 | 15 | 1.5 |
| Example P4 | 30,800 | 17 | 1.5 |

Figure 22:
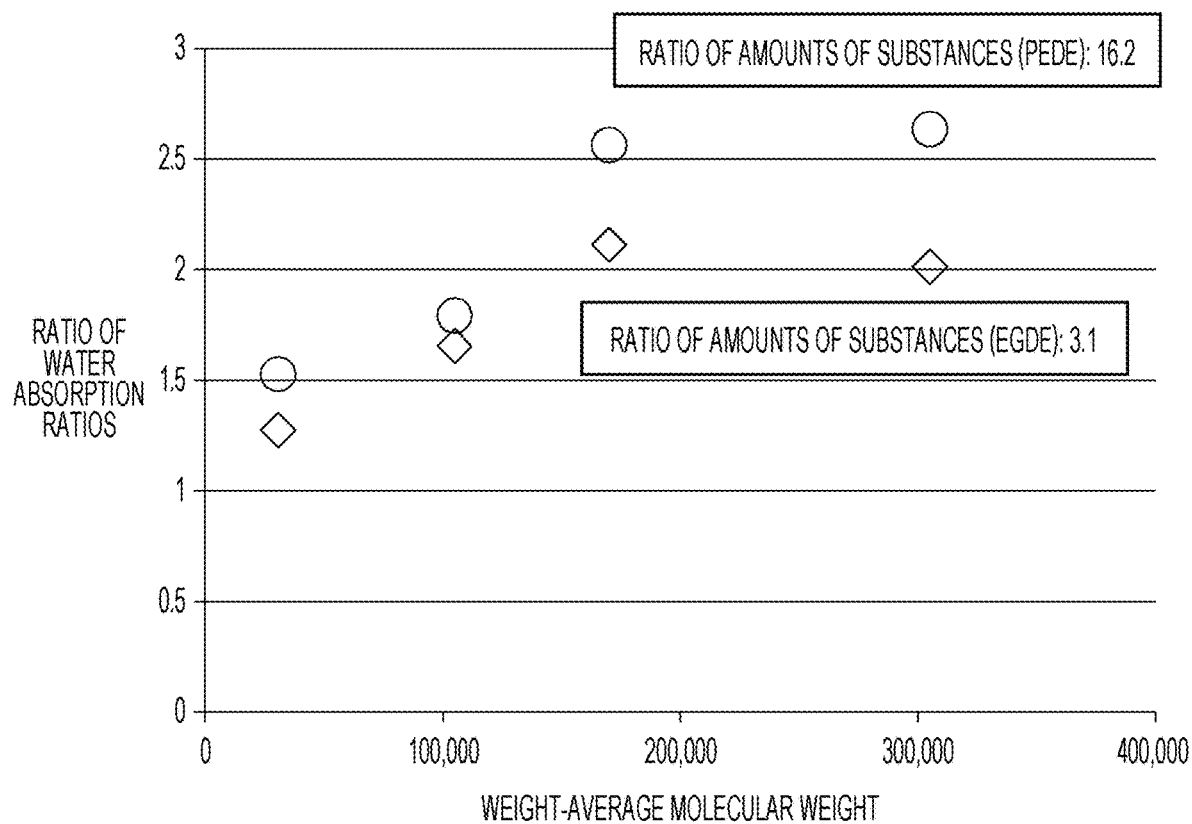
FIG. 22 is a graph that shows relationship between weight-average molecular weights of cellulose used as raw materials and ratios of water absorption ratios relating to Example E1-4 and Example E2 to Example E4, as well as Example P1-6 and Example P2 to Example P4.

FIG. 22 is a graph showing the relationship between weight-average molecular weights of cellulose used as raw materials and ratios of water absorption ratios relating to Example E1-4 and Example E2 to Example E4, as well as Example P1-6 and Example P2 to Example P4. Here, the "ratio of water absorption ratios" means an amount obtained by dividing a water absorption ratio relating to a crosslinked cellulose sheet by the water absorption ratio relating to the corresponding cellulose sheet in which cellulose used as a raw material has the same weight-average molecular weight but a crosslinked structure is not formed. For example, the ratio of water absorption ratios of Example E1-4 can be obtained by dividing the water absorption ratio of Example E1-4 by the water absorption ratio of Comparative Example C1-1, and the ratio of water absorption ratios of Example P2 can be obtained by dividing the water absorption ratio of Example P2 by the water absorption ratio of Comparative Example C2. In FIG. 22, a white diamond "◇" is a plot of each of the ratios of water absorption ratios relating to each of Example E1-4 and Example E2 to Example E4 in which EGDE was used as a cross-linking reagent, and a white circle "○" is a plot of each of the ratios of water absorption ratios relating to each of Example P1-6 and Example P2 to Example P4 in which PEDE was use as a cross-linking reagent.

From FIG. 22, it can be understood that in both cases when each of EGDE and PEDE was used as a cross-linking reagent, as the weight-average molecular weight of cellulose increases, the ratio of water absorption ratios tends to increase, and when the weight-average molecular weight becomes equal to or higher than 170,000, an approximately constant high ratio of water absorption ratios tends to be exhibited. From the above, from the viewpoint of obtaining a higher water absorption ratio, when the ratio of amount of substance of a cross-linking reagent to the amount of substance of cellulose in terms of the glucose residue is the same, it can be understood that the use of cellulose having a larger weight-average molecular weight is more advantageous. It can be said that the length of the molecular chain of the cross-linking reagent does not largely affect this property.

Example E1-8

A crosslinked cellulose sheet of Example E1-8 was prepared in the same manner as Example E1-4 (the ratio of amounts of substances: 3.1, crosslinking point carbon ratio: 11.9%) except that the gelling step of the liquid film was not performed. The thickness d and the bulk density $d_B$ measured in the same manner as Example E1-1 were 14 μm and 1.5 g/cm³, respectively.

Example P1-10

A crosslinked cellulose sheet of Example P1-10 was prepared in the same manner as Example P1-6 (the ratio of amounts of substances: 16.2, crosslinking point carbon ratio: 11.7%) except that the gelling step of the liquid film was not performed. The thickness d and the bulk density $d_B$ measured in the same manner as Example E1-1 were 17 μm and 1.5 g/cm³, respectively.

Comparative Example C1-8

A cellulose sheet of Comparative Example C1-8 was prepared in the same manner as Example E1-8 except that the formation of the crosslinked structure by using EGDE was not performed. The thickness d and the bulk density $d_B$ measured in the same manner as Example E1-1 were 16 μm and 1.5 g/cm³, respectively.

Table 5 below shows the thicknesses d and the bulk densities $d_B$ of cellulose sheets obtained in the same manner as the sample of Example E1-1, relating to each sample of Example E1-8, Example P1-10 and Comparative Example C1-8 in combination. Meanwhile, Table 5 shows, for the convenience of comparison, the measurement results of the thicknesses d and the bulk densities $d_B$ relating to Example E1-4 and Example P1-6 in combination.

TABLE 5

| Sample | Gelling step | Step of formation of crosslinked structure | Thickness d (μm) | Bulk density $d_B$ (g/cm³) |
|---|---|---|---|---|
| Example E1-4 | Present | Present (EGDE) | 14 | 1.5 |
| Example E1-8 | Absent | Present (EGDE) | 14 | 1.5 |
| Example P1-6 | Present | Present (PEDE) | 16 | 1.5 |
| Example P1-10 | Absent | Present (PEDE) | 17 | 1.5 |
| Comparative Example C1-8 | Absent | Absent | 16 | 1.5 |

Figure 23:
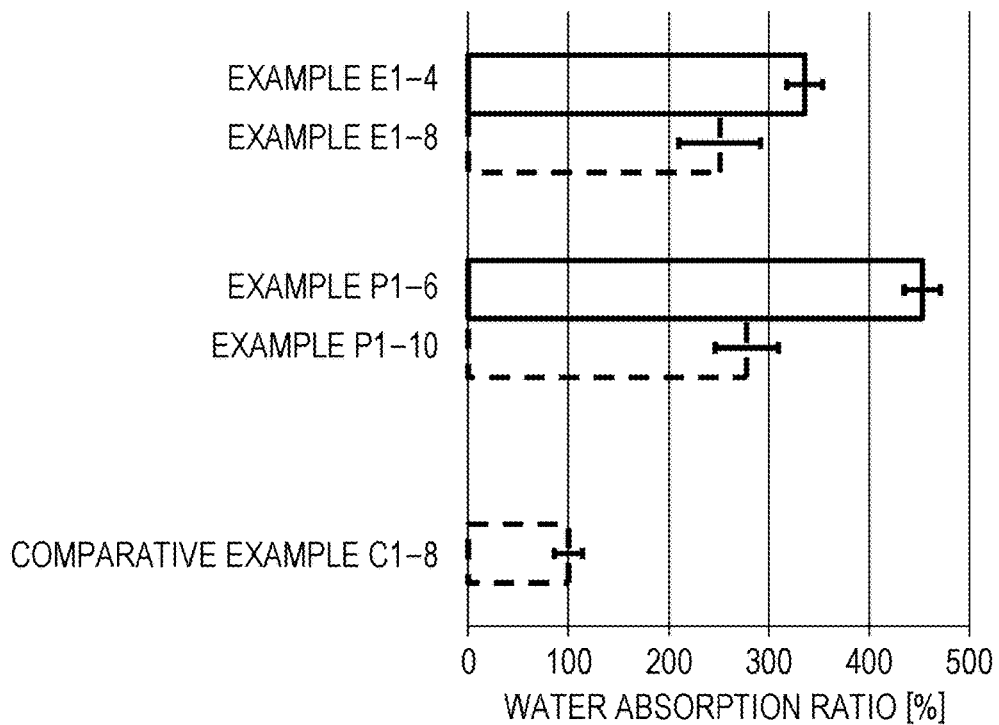
FIG. 23 is a graph that shows measurement results of water absorption ratios relating to Example E1-4, Example E1-8, Example P1-6, Example P1-10 and Comparative Example C1-8.

FIG. 23 is a graph showing measurement results of water absorption ratios relating to Example E1-4, Example E1-8, Example P1-6, Example P1-10 and Comparative Example C1-8. In FIG. 23, graphs by broken lines represent measurement results relating to the samples in which no gelling step was performed. Meanwhile, each of plots of water absorption ratios shown in FIG. 23 is the mean value of five cellulose sheets.

As understood from FIG. 23, by forming a crosslinked structure in cellulose by using a cross-linking reagent, an effect of improving the water absorption ratio can be exhibited. In addition, it can be understood that in the case when each of EGDE and PEDE was used as a cross-linking reagent, the water absorption ratio can be further improved by subjecting the liquid film containing cellulose to the gelling step.

Example E5-1

A crosslinked cellulose sheet of Example E5-1 was prepared in the same manner as Example E1-1 (the ratio of amounts of substances: 0.016) except that freeze drying was applied instead of vacuum drying in the step of drying the crosslinked gel. Freeze drying was performed according to the following procedure.

The crosslinked gel after washing was immersed in tert-butyl alcohol, and the rinse liquid in the crosslinked gel was substituted with tert-butyl alcohol. After that, tert-butyl alcohol was frozen at a temperature of −60° C. The crosslinked gel was disposed in a vacuum vessel, and deaeration inside the vacuum vessel to 2 Pa was performed to obtain the crosslinked cellulose sheet of Example E5-1. The thickness d and the bulk density $d_B$ of the crosslinked cellulose sheet obtained in the same manner as the sample of Example E1-1 were 225 μm and 0.13 g/cm³, respectively. It was possible to obtain a polymer sheet having a low bulk density.

Example E5-2 to Example E5-9

A crosslinked cellulose sheet of each of Example E5-2 to Example E5-9 was prepared in the same manner as Example E5-1 except that the ratio of amounts of substances was changed. Table 6 below shows the ratios of amounts of substances, the crosslinking point carbon ratios CR, the thicknesses d and the bulk densities $d_B$ of the crosslinked cellulose sheets obtained in the same manner as the sample of Example E1-1 relating to each sample of Example E5-1 to Example E1-11 in combination.

TABLE 6

| Sample | Ratio of amount of substance of EDGE to amount of substance in terms of glucose residue | Crosslinking point carbon ratio CR (%) | Thickness d (μm) | Bulk density $d_B$ (g/cm³) |
|---|---|---|---|---|
| Example E5-1 | 0.016 | 0.58 | 225 | 0.13 |
| Example E5-2 | 0.078 | 1.49 | 214 | 0.14 |
| Example E5-3 | 0.78 | 6.11 | 232 | 0.17 |
| Example E5-4 | 1.6 | 8.72 | 237 | 0.16 |
| Example E5-5 | 3.1 | 11.85 | 234 | 0.14 |
| Example E5-6 | 6.2 | 17.41 | 248 | 0.12 |
| Example E5-7 | 9.3 | 19.78 | 221 | 0.17 |
| Example E5-8 | 15.5 | 24.21 | 236 | 0.18 |
| Example E5-9 | 139.5 | 43.36 | 251 | 0.18 |

Figure 24:
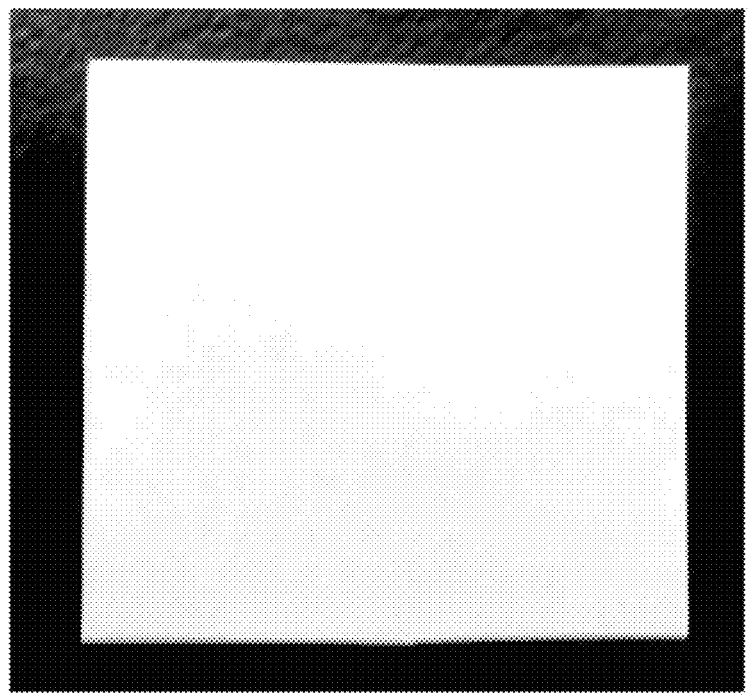
FIG. 24 is a view that represents a photograph showing one example of appearance of a crosslinked cellulose sheet.
Figure 25:
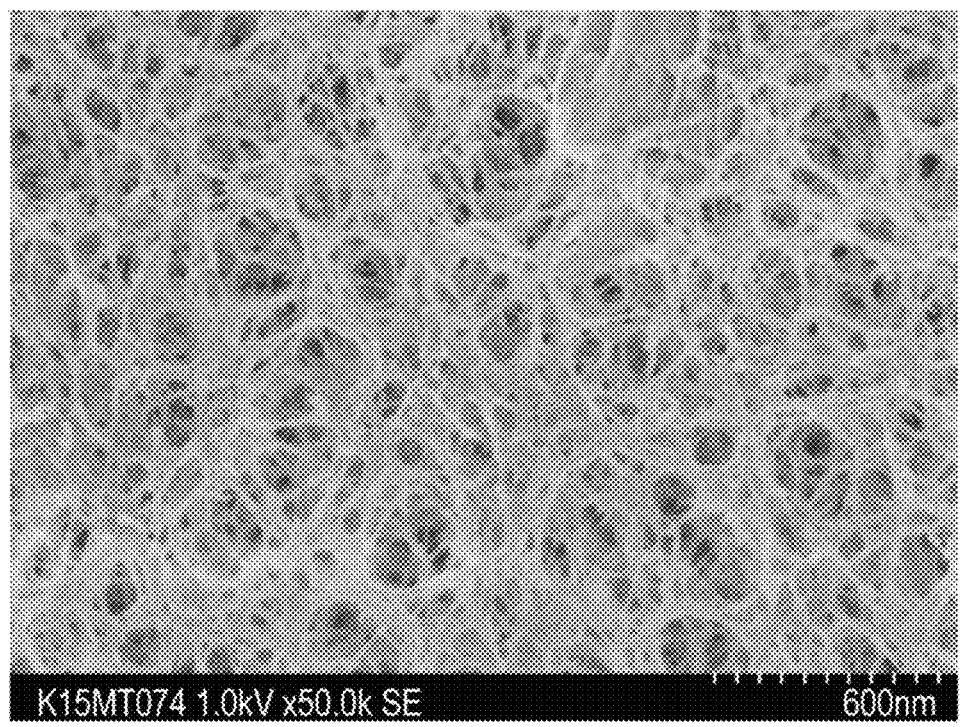
FIG. 25 is a view that represents an SEM image showing one example of a magnified cross section of a crosslinked cellulose sheet.

FIG. 24 shows the appearance of the crosslinked cellulose sheet of Example E5-1, and FIG. 25 shows a magnified cross section of the crosslinked cellulose sheet of Example E5-5. The cross section image of the sample was acquired by using a scanning electron microscope S-5500 manufactured by Hitachi High-Technologies Corporation on a sample for cross-sectional observation prepared by cryogenic processing using broad ion beam (BIB).

Example P5-1

A crosslinked cellulose sheet of Example P5-1 was prepared in the same manner as Example P1-1 except that freeze drying was applied instead of vacuum drying in the drying step of the crosslinked gel. The crosslinking point carbon ratio CR was obtained in the same manner as the sample of Example E1-1, and was 0.88%. In addition, the thickness d and the bulk density $d_B$ of the obtained crosslinked cellulose sheet were 248 μm and 0.14 g/cm³, respectively.

Example P5-2 to Example P5-10

A crosslinked cellulose sheet of each of Example P5-2 to Example P5-10 was prepared in the same manner as Example P5-1 except that the ratio of amounts of substances was changed. Table 7 below shows, the ratios of amounts of substances, the crosslinking point carbon ratios CR, the thicknesses d and the bulk densities $d_B$ of the crosslinked cellulose sheets obtained in the same manner as the sample of Example E1-1 relating to each sample of Example P5-1 to Example P5-10 in combination.

TABLE 7

| Sample | Ratio of amount of substance of PEDE to amount of substance in terms of glucose residue | Crosslinking point carbon ratio CR (%) | Thickness d (μm) | Bulk density $d_B$ (g/cm³) |
|---|---|---|---|---|
| Example P5-1 | 1.1 | 0.88 | 248 | 0.14 |
| Example P5-2 | 2.16 | 2.63 | 225 | 0.13 |
| Example P5-3 | 5.40 | 5.47 | 234 | 0.17 |
| Example P5-4 | 10.80 | 8.81 | 249 | 0.14 |
| Example P5-5 | 13.50 | 9.73 | 265 | 0.12 |
| Example P5-6 | 16.20 | 11.74 | 274 | 0.17 |
| Example P5-7 | 18.90 | 13.72 | 247 | 0.17 |
| Example P5-8 | 21.60 | 14.33 | 241 | 0.18 |
| Example P5-9 | 27.00 | 17.74 | 257 | 0.14 |
| Example P5-10 | 48.60 | 25.37 | 247 | 0.18 |

Figure 26:
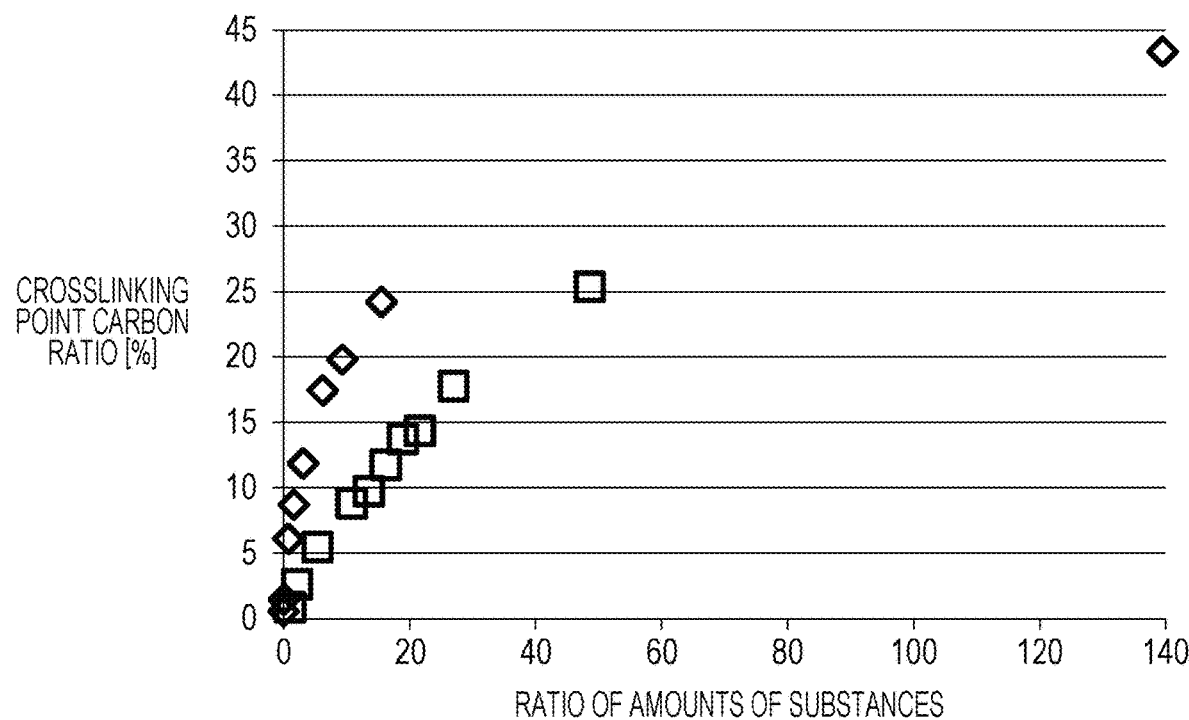
FIG. 26 is a graph that shows relationship between ratios of amounts of substances and crosslinking point carbon ratios with regard to Example E5-1 to Example E5-9 and Example P5-1 to Example P5-10.

FIG. 26 is a graph showing the relationship between the ratios of amounts of substances and the crosslinking point carbon ratios with regard to Example E5-1 to Example E5-9 and Example P5-1 to Example P5-10. In FIG. 26, a white diamond "◇" is a plot relating to each of Example E5-1 to Example E5-9 in which EGDE was used as the cross-linking reagent, and a white square "□" is a plot relating to Example P1-1 to Example P5-10 in which PEDE was used as the cross-linking reagent. From FIG. 26, it can be understood that in both cases where EGDE was used as the cross-linking reagent and PEDE was used as the cross-linking reagent, the crosslinking point carbon ratio tends to increase when the ratio of amounts of substances increases in the same manner as the cases in which vacuum drying was applied (see FIG. 18).

Comparative Example C5-1

A cellulose sheet of Comparative Example C5-1 was prepared in the same manner as Example E5-1 except that the formation of the crosslinked structure by using EGDE was not performed. The thickness d and the bulk density $d_B$ measured in the same manner as Example E1-1 were 239 μm and 0.16 g/cm³, respectively.

Figure 27:
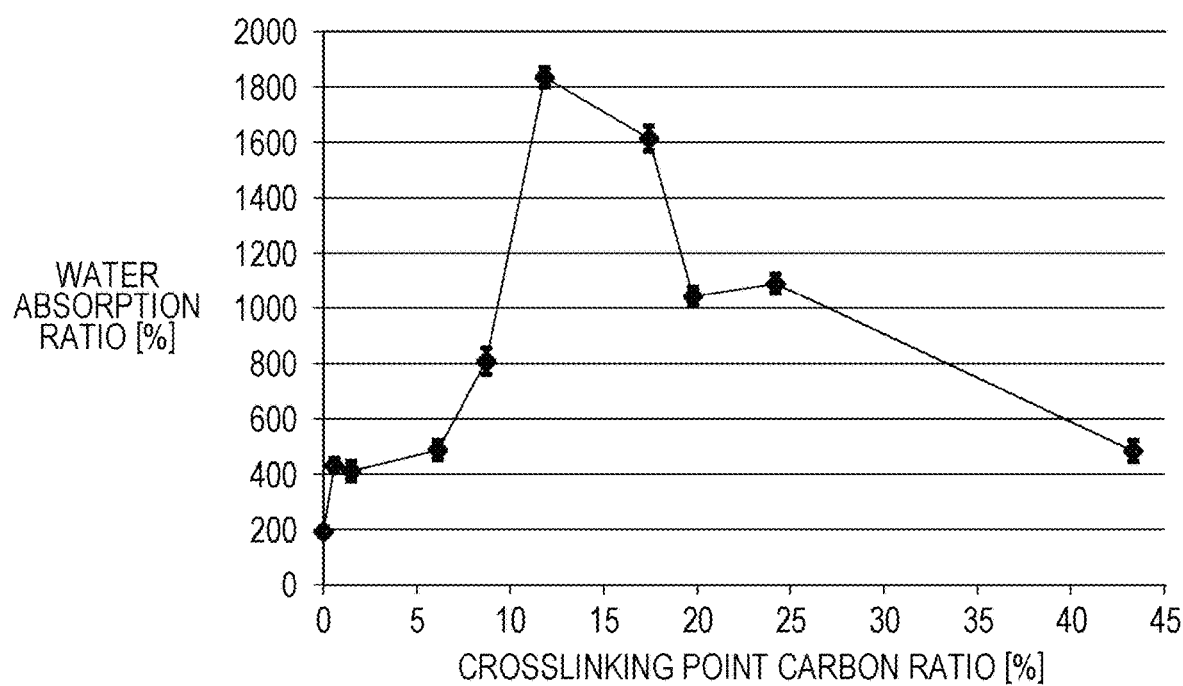
FIG. 27 is a graph that shows relationship between crosslinking point carbon ratios and water absorption ratios relating to Example E5-1 to Example E5-9 and Comparative Example C5-1.

FIG. 27 is a graph showing the relationship between crosslinking point carbon ratios and water absorption ratios relating to Example E5-1 to Example E5-9 and Comparative Example C5-1. Meanwhile, each of plots of water absorption ratios shown in FIG. 27 is the mean value of five cellulose sheets.

From FIG. 27, it can be understood that when the crosslinking point carbon ratio is equal to or higher than about 0.58% (the ratio of amounts of substances can be said to be equal to or higher than about 0.016), a crosslinked cellulose sheet having a higher water absorption ratio as compared with the cellulose sheet having no crosslinked structure (Comparative Example C5-1) can be obtained. It can be understood with reference to FIG. 27 that when the crosslinking point carbon ratio is 11.9% (at this time, the ratio of amounts of substances is 3.1), the maximum water absorption ratio is exhibited, and when the crosslinking point carbon ratio is within a range from about 6.1 to about 19.8%, inclusive, an especially high water absorption ratio can be obtained. In other words, when the ratio of amounts of substances is within a range from about 0.78 to about 9.3, inclusive, an especially high water absorption ratio can be obtained. In addition, from FIG. 27 and the above-described FIG. 20, in the both cases where vacuum drying and freeze drying were employed, it can be understood that an effect of improving the absorption ratio can be obtained by the formation of the crosslinked structure.

Figure 28:
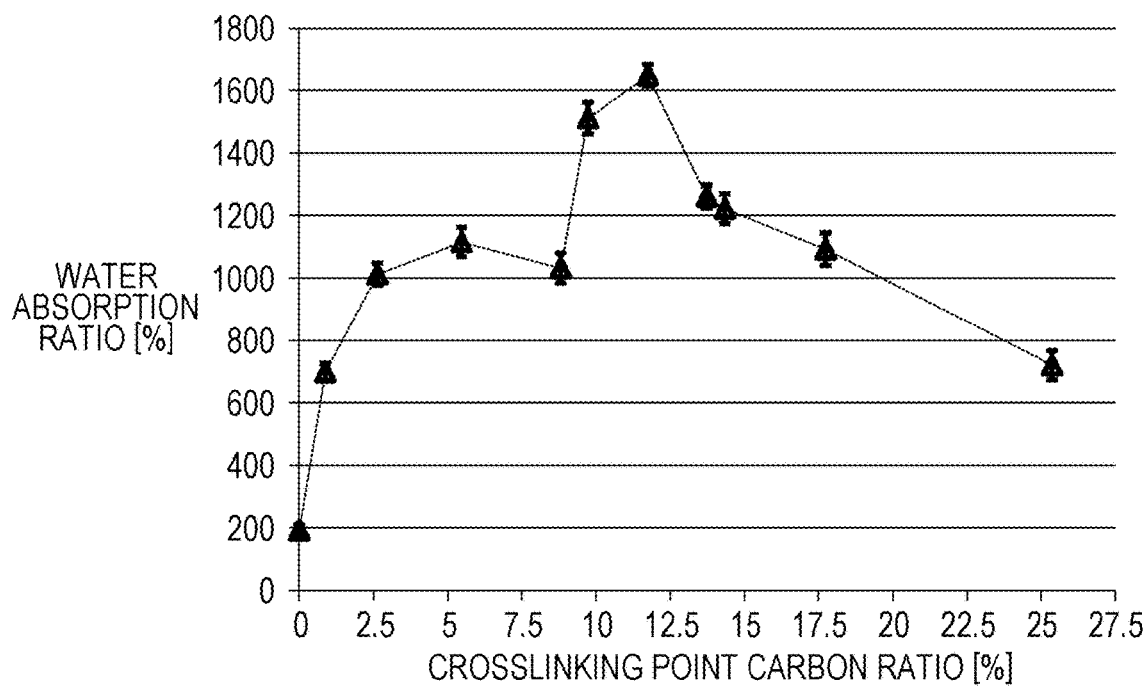
FIG. 28 is a graph that shows relationship between crosslinking point carbon ratios and water absorption ratios relating to Example P5-1 to Example P5-10 and Comparative Example C5-1.

FIG. 28 is a graph showing the relationship between crosslinking point carbon ratios and water absorption ratios relating to Example P5-1 to Example P5-10 and Comparative Example C5-1. Meanwhile, each plot of water absorption ratios shown in FIG. 16 is the mean value of five cellulose sheets.

From FIG. 28, it can be understood that when the crosslinking point carbon ratio is equal to or higher than about 0.88% (the ratio of amounts of substances can be said to be equal to or higher than about 1.1), a crosslinked cellulose sheet having a higher water absorption ratio as compared with the cellulose sheet having no crosslinked structure (Comparative Example C5-1) can be obtained. It can be understood with reference to FIG. 28 that when the crosslinking point carbon ratio is 11.7% (at this time, the ratio of amounts of substances is 16.2), the maximum water absorption ratio is exhibited, and when the crosslinking point carbon ratio is within a range from about 8.8% to about 17.7%, inclusive, an especially high water absorption ratio can be obtained. In other words, when the ratio of amounts of substances is within a range from about 10.8 to about 27.0, inclusive, an especially high water absorption ratio can be obtained. In addition, from FIG. 28 and the above-described FIG. 21, in the both cases where vacuum drying and freeze drying were employed, it can be understood that an effect of improving the absorption ratio can be obtained by the formation of the crosslinked structure.

From the comparison between FIG. 27 and FIG. 20, as well as the comparison between FIG. 28 and FIG. 21, it can be understood that when the crosslinking point carbon ratio is the same, a crosslinked cellulose sheet obtained by applying freeze drying tends to show a higher absorption ratio than a crosslinked cellulose sheet obtained by applying vacuum drying. In other words, from the viewpoint of obtaining a higher absorption ratio, the application of freeze drying is more advantageous than that of vacuum drying. It is assumed that it is because larger voids in a crosslinked cellulose tend to be formed by applying freeze drying.

Example E6 to Example E8

A crosslinked cellulose sheet of each of Example E6 to Example E8 was prepared in the same manner as Example E5-5 (the ratio of amounts of substances: 3.1, crosslinking point carbon ratio: 11.9%) except that a cellulose solution was prepared by using cellulose having a different weight-average molecular weight.

Comparative Example C6 to Comparative Example C8

A cellulose sheet of each of Comparative Example C6 to Comparative Example C8 was prepared in the respectively same manner as Example E6 to Example E8 except that the formation of a crosslinked structure by using EGDE was not performed.

Table 8 below shows weight-average molecular weights of cellulose used as raw materials, the thicknesses d and the bulk densities $d_B$ of cellulose sheets obtained in the same manner as the sample of Example E1-1 relating to each sample of Example E6 to Example E8 and Comparative Example C6 to Comparative Example C8 in combination.

TABLE 8

| Sample | Weight-average molecular weight | Thickness d (μm) | Bulk density $d_B$ (g/cm³) |
|---|---|---|---|
| Example E6 | 170,000 | 234 | 0.15 |
| Example E7 | 105,000 | 225 | 0.17 |
| Example E8 | 30,800 | 211 | 0.14 |
| Comparative Example C6 | 170,000 | 234 | 0.14 |
| Comparative Example C7 | 105,000 | 224 | 0.15 |
| Comparative Example C8 | 30,800 | 248 | 0.18 |

Example P6 to Example P8

A crosslinked cellulose sheet of each of Example P6 to Example P8 was prepared in the same manner as Example P5-6 (the ratio of amounts of substances: 16.2, crosslinking point carbon ratio: 11.7%) except that a cellulose solution was prepared by using cellulose having a different weight-average molecular weight.

Table 9 below shows weight-average molecular weights of cellulose used as raw materials, the thicknesses d and the bulk densities $d_B$ of cellulose sheets obtained in the same manner as the sample of Example E1-1 relating to each sample of Example P6 to Example P8 in combination.

TABLE 9

| Sample | Weight-average molecular weight | Thickness d (μm) | Bulk density $d_B$ (g/cm³) |
|---|---|---|---|
| Example P6 | 170,000 | 245 | 0.14 |
| Example P7 | 105,000 | 248 | 0.13 |
| Example P8 | 30,800 | 221 | 0.16 |

Figure 29:
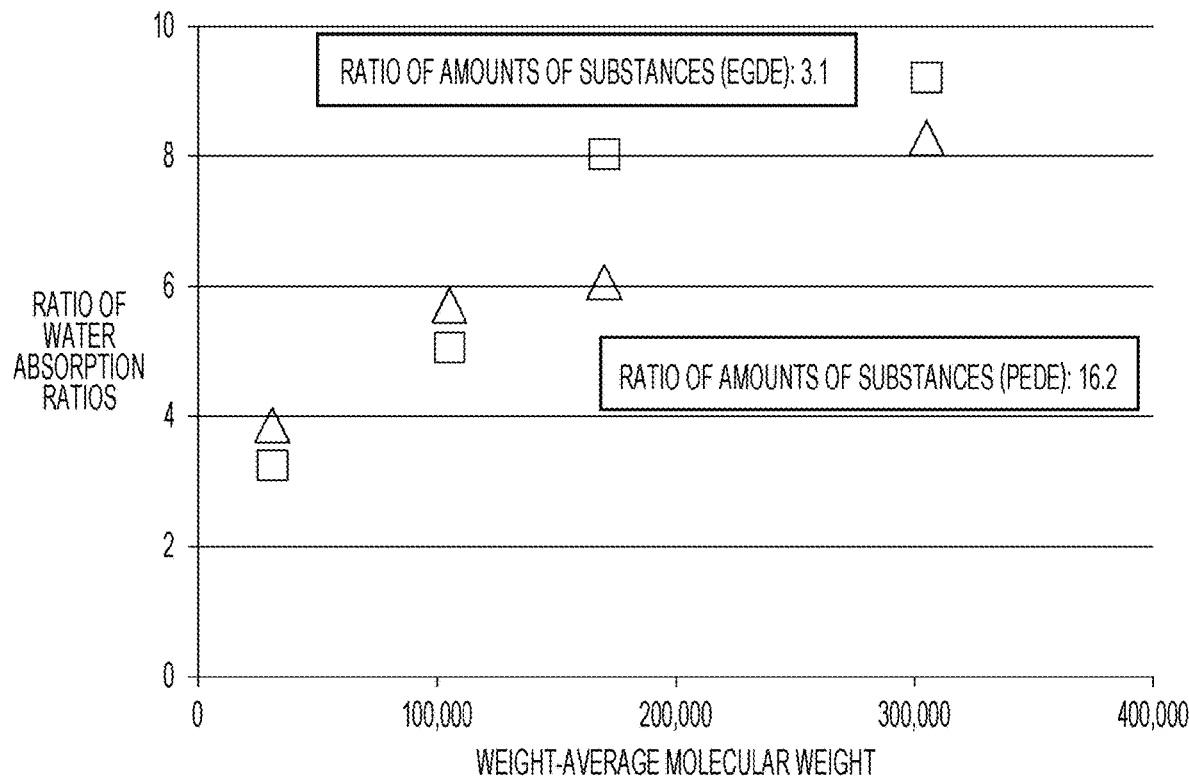
FIG. 29 is a graph that shows relationship between weight-average molecular weights of cellulose used as raw materials and ratios of water absorption ratios relating to Example E5-5 and Example E6 to Example E8, as well as Example P5-6 and Example P6 to Example P8.

FIG. 29 is a graph showing the relationship between weight-average molecular weights of cellulose used as raw materials and the ratios of water absorption ratios relating to Example E5-5 and Example E6 to Example E8, as well as Example P5-6 and Example P6 to Example P8. In FIG. 29, a white square "□" is a plot relating to the ratio of water absorption ratios relating to Example E5-5 and Example E6 to Example E8, in which EGDE was used as the cross-linking reagent, and white triangle "Δ" is a plot relating to the ratio of water absorption ratios relating to Example P5-6 and Example P6 to Example P8, in which PEDE was used as the cross-linking reagent.

From FIG. 29, it can be understood that in both the cases where EGDE and PEDE were used as the cross-linking reagents, when the weight-average molecular weight of cellulose increases, the ratio of water absorption ratios increases, and when the weight-average molecular weight becomes equal to or higher than 170,000, an approximately constant high ratio of water absorption ratios tends to be exhibited. From this finding, it can be understood that from the viewpoint of obtaining a higher water absorption ratio, when the ratio of amount of substance of a cross-linking reagent to the amount of substance of cellulose in terms of the glucose residue is the same, it is more advantageous to use cellulose having a higher weight-average molecular weight.

In addition, from the comparison between FIG. 29 and the above-described FIG. 22, it can be understood that a cross-linked cellulose sheet is capable of showing a different ratio of water absorption ratios according to the drying method even when cellulose used as raw materials have the same weight-average molecular weight. When comparing FIG. 29 and FIG. 22, in the case when cellulose has the same weight-average molecular weight, a crosslinked sheet to which freeze drying was applied shows a higher ratio of absorption ratios than a crosslinked sheet to which vacuum drying was applied. It is assumed that this is because by applying freeze drying, larger voids are formed in a cross-linked cellulose, a bulk density decreases, and as a result, a crosslinked cellulose sheet having a higher absorption ratio can be obtained. However, even in the case where vacuum drying was applied, when cellulose used as raw materials has a weight-average molecular weight of equal to or higher than 170,000, a higher absorption ratio can be realized, which is the same as the case where freeze drying was applied.

Example E9-1 to Example E9-10

A crosslinked cellulose sheet of Example E9-1 to Example E9-10 was prepared in the same manner as Example E5-5 (the ratio of amounts of substances: 3.1) except that in the step of drying a crosslinked gel, as a solvent for substituting a rinse liquid in the crosslinked gel, a mixed solvent of tert-butyl alcohol and ethanol or ethanol was used. Table 10 below shows mass ratios of tert-butyl alcohol and ethanol, the thicknesses d and the bulk densities $d_B$ of cellulose sheets obtained in the same manner as the sample of Example E1-1 relating to each sample of Example E1-1 to Example E1-10 in combination.

TABLE 10

| Sample | Butyl alcohol: ethanol (mass ratio) | Thickness d (μm) | Bulk density $d_B$ (g/cm³) |
|---|---|---|---|
| Example E9-1 | 9:1 | 214 | 0.16 |
| Example E9-2 | 8:2 | 198 | 0.21 |
| Example E9-3 | 7:3 | 175 | 0.29 |
| Example E9-4 | 6:4 | 145 | 0.37 |
| Example E9-5 | 5:5 | 129 | 0.46 |
| Example E9-6 | 4:6 | 104 | 0.67 |
| Example E9-7 | 3:7 | 84 | 0.83 |
| Example E9-8 | 2:8 | 64 | 0.93 |
| Example E9-9 | 1:9 | 34 | 1.3 |
| Example E9-10 | 0:10 | 16 | 1.5 |

Example P9-1 to Example P9-10

A crosslinked cellulose sheet of Example P9-1 to Example P9-10 was prepared in the same manner as Example P5-6 (the ratio of amounts of substances: 16.2) except that in the step of drying a crosslinked gel, as a solvent for substituting a rinse liquid in the crosslinked gel, a mixed solvent of tert-butyl alcohol and ethanol or ethanol was used. Table 11 below shows mass ratios of tert-butyl alcohol and ethanol, the thicknesses d and the bulk densities $d_B$ of cellulose sheets obtained in the same manner as the sample of Example E1-1 relating to each sample of Example P1-1 to Example P1-10 in combination.

| Sample | Butyl alcohol: ethanol (mass ratio) | Thickness d (μm) | Bulk density $d_B$ (g/cm³) |
|---|---|---|---|
| Example P9-1 | 9:1 | 256 | 0.21 |
| Example P9-2 | 8:2 | 238 | 0.25 |
| Example P9-3 | 7:3 | 214 | 0.34 |
| Example P9-4 | 6:4 | 188 | 0.41 |
| Example P9-5 | 5:5 | 154 | 0.53 |
| Example P9-6 | 4:6 | 125 | 0.72 |
| Example P9-7 | 3:7 | 101 | 0.89 |
| Example P9-8 | 2:8 | 79 | 0.97 |
| Example P9-9 | 1:9 | 34 | 1.3 |
| Example P9-10 | 0:10 | 14 | 1.5 |

From Tables 10 and 11, it can be understood that the bulk density of the crosslinked cellulose sheet varies depending on the ratio of ethanol included in the solvent for substituting the rinse liquid. In addition, it can be also understood that when the ratio of ethanol in the solvent increases, the bulk density of the crosslinked cellulose sheet increases. It is assumed that this is because when the ratio of ethanol in the solvent increases, the freezing point of the solvent decreases, which causes the solvent being hard to freeze, and as a result, voids tend to be hard to form in the crosslinked gel.

Figure 30:
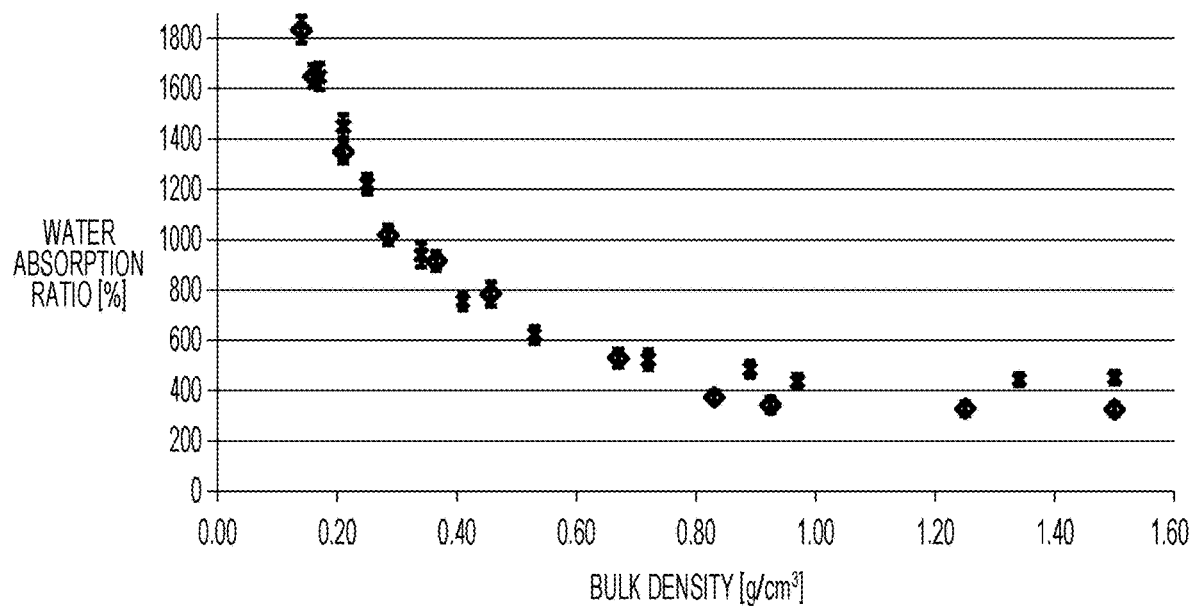
FIG. 30 is a graph that shows relationship between bulk densities and water absorption ratios relating to Example E5-5 and Example E9-1 to Example E9-10, as well as Example P5-6 and Example P9-1 to Example P9-10.

FIG. 30 is a graph showing the relationship between the bulk density and the water absorption ratio relating to Example E5-5 and Example E9-1 to Example E9-10, as well as, Example P5-6 and Example P9-1 to Example P9-10. In FIG. 30, a white diamond "◇" is a plot of the water absorption ratio in the case where EGDE was used as a cross-linking reagent relating to Example E5-5 and Example E9-1 to Example E9-10, and an asterisk "*" is a plot of the water absorption ratio in the case where PEDE was used as a cross-linking reagent relating to Example P5-6 and Example P9-1 to Example P9-10.

With reference to FIG. 30, in both the cases where EGDE and PEDE were used as the cross-linking reagent, the water absorption ratio is approximately constant in a range of the bulk density exceeding about 0.9 g/cm³, whereas in a range of the bulk density equal to or lower than about 0.9 g/cm³, when the bulk density decreases, the absorption ratio tends to increase. From the above, it can be understood that by making a bulk density of a crosslinked cellulose be equal to or lower than about 0.9 g/cm³, it is possible to improve the water absorption ratio further.

Example E10

A crosslinked cellulose sheet of Example E10 was prepared in the same manner as Example E5-5 (the ratio of amounts of substances: 3.1, crosslinking point carbon ratio: 11.9%) except that the gelling step of the liquid film was not performed.

Example P10

A crosslinked cellulose sheet of Example P10 was prepared in the same manner as Example P5-6 (the ratio of amounts of substances: 16.2, crosslinking point carbon ratio: 11.7%) except that the gelling step of the liquid film was not performed.

Comparative Example C10

A cellulose sheet of Comparative Example C10 was prepared in the same manner as Example E10 except that the formation of a crosslinked structure by using EGDE was not performed.

Table 12 below shows measurement results of the water absorption ratios $A_w$ relating to each sample of Example E10, Example P10 and Comparative Example C10. Meanwhile, Table 12 shows measurement results of the water absorption ratios $A_w$ relating to Example E5-5 and Example P5-6 in combination for the convenience of comparison.

TABLE 12

| Sample | Gelling step | Step of formation of crosslinked structure | Water absorption ratio $A_w$ (%) |
|---|---|---|---|
| Example E5-5 | Present | Present (EGDE) | 1835 |
| Example E10 | Absent | Present (EGDE) | 1614 |
| Example P5-6 | Present | Present (PEDE) | 1648 |
| Example P10 | Absent | Present (PEDE) | 1432 |
| Comparative Example C10 | Absent | Absent (EGDE) | 141 |

Figure 31:
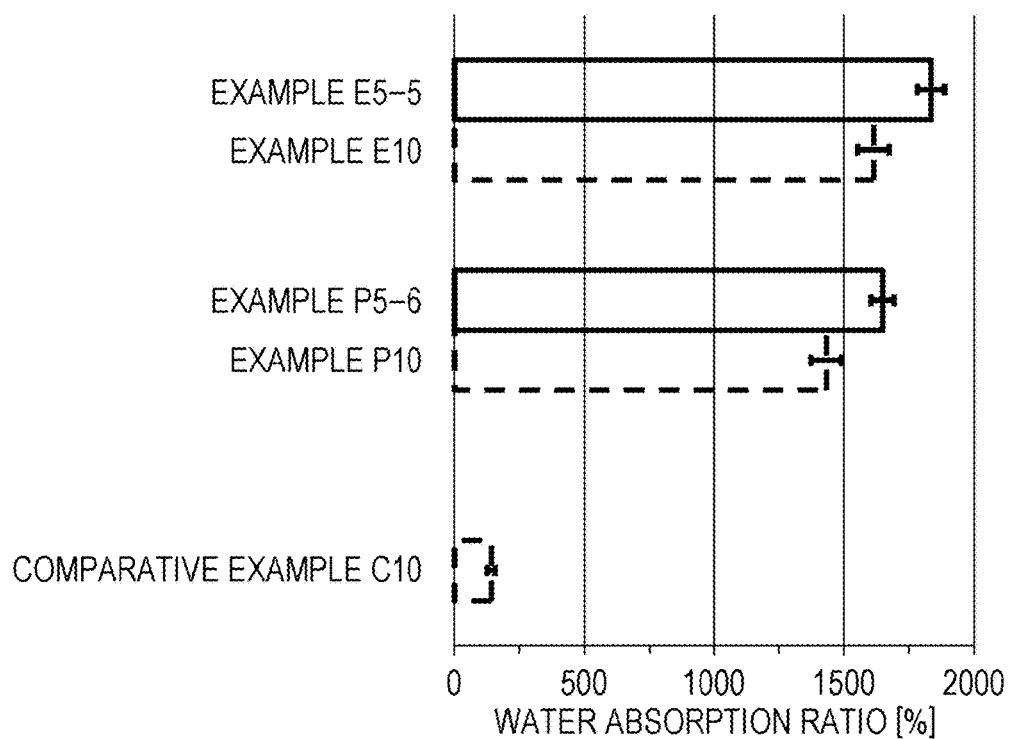
FIG. 31 is a graph that shows measurement results of water absorption ratios relating to Example E5-5, Example E10, Example P5-6, Example P10 and Comparative Example C10.

FIG. 31 is a graph showing measurement results of the water absorption ratios relating to Example E5-5, Example E10, Example P5-6, Example P10 and Comparative Example C10. In FIG. 31, a graph by a broken line represents the measurement result relating to the sample on which no gelling step was performed. Meanwhile, each plot of the water absorption ratios shown in FIG. 31 is the mean value of five cellulose sheets.

From Table 12 and FIG. 31, it can be understood that in the case where freeze drying was applied, an effect of improving the water absorption ratio is obtained by the formation of the crosslinked structure in cellulose by using the cross-linking reagent. In addition, in both the cases where EGDE and PEDE were used as the cross-linking reagents, it can be understood that it is possible to improve the water absorption ratio further by undergoing the gelling step of the liquid film containing cellulose.

Evaluation of Mechanical Strengths by Tensile Testing

Next, the mechanical strengths of the sample were evaluated by tensile testing. Here, as indicators of the mechanical strengths, measurements of the elastic modulus, tensile strength and elongation of a sheet at a dried state and a water-absorbed state were performed. The elastic modulus, tensile strength and elongation of a sheet were capable of being measured by a method in accordance with JIS K 7161. For measuring the tensile strength, for example, a compact tabletop tester EZ-Test manufactured by Shimadzu Corporation was used to perform measurements on a plurality of test pieces under conditions of: temperature: 23° C., distance between chucks: 20 mm, and tension speed: 100 mm/min, and the mean value was used for evaluation. For the measurements relating to a dried state, the sample dried in an environment of 0.02 MPa and 90° C. for equal to or longer than 2 hours was cut into the shape of No. 7 test piece for use. For the measurements relating to a water-absorbed state, a test piece was set in the tester, and thereafter, the sample was made to absorb sufficient water by spraying water to the surface of the sample, and immediately after wiping water droplets on the surface of the sample, tensile testing was started.

Tables 13 and 14 below show the results of the tensile testing relating to each of sheets of Example E1-4 (the ratio of amounts of substances: 3.1) that showed a relatively high water absorption ratio among Example E1-1 to Example E1-7, Example P1-6 (the ratio of amounts of substances: 16.2) that showed a relatively high water absorption ratio among Example P1-1 to Example P1-9, and Comparative Example C1-1. Meanwhile, Table 13 shows measurement results in a dried state and Table 14 shows measurement results in a water-absorbed state.

TABLE 13

| Sample | Cross-linking reagent | Ratio of amounts of substances | Drying method | Dried state |||
|---|---|---|---|---|---|---|
| | | | | Elastic modulus (GPa) | Tensile strength (MPa) | Elongation (%) |
| Example E1-4 | EGDE | 3.10 | Vacuum drying | 7.31 ± 0.75 | 138.74 ± 5.62 | 5.21 ± 0.98 |
| Example P1-6 | PEDE | 16.20 | Vacuum drying | 6.54 ± 0.98 | 128.56 ± 4.12 | 5.11 ± 0.87 |
| Comparative Example C1-1 | — | — | Vacuum drying | 5.21 ± 0.49 | 100.71 ± 5.21 | 4.72 ± 0.73 |

TABLE 14

| Sample | Cross-linking reagent | Ratio of amounts of substances | Drying method | Water-absorbed state |||
|---|---|---|---|---|---|---|
| | | | | Elastic modulus (GPa) | Tensile strength (MPa) | Elongation (%) |
| Example E1-4 | EGDE | 3.10 | Vacuum drying | 0.0636 ± 0.0074 | 23.20 ± 1.85 | 24.00 ± 2.15 |
| Example P1-6 | PEDE | 16.20 | Vacuum drying | 0.0756 ± 0.0067 | 20.56 ± 2.42 | 23.12 ± 2.12 |
| Comparative Example C1-1 | — | — | Vacuum drying | 0.1321 ± 0.0081 | 7.525 ± 1.56 | 14.31 ± 1.87 |

Reference is made to Table 13. With regard to samples in a dried state, in the both cases where EGDE and PEDE were used as the cross-linking reagents, the elastic modulus, tensile strength and elongation were improved as compared with a cellulose sheet having no crosslinked structure. Reference is made to Table 14. With regard to samples in a water-absorbed state, in the both cases where EGDE and PEDE were used as the cross-linking reagents, the elastic modulus was slightly decreased, but the tensile strength and elongation were improved as compared with a cellulose sheet having no crosslinked structure.

Tables 15 and 16 below show measurement results of the tensile testing relating to each of sheets of Example E5-5 (the ratio of amounts of substances: 3.1) that showed a relatively high water absorption ratio among Example E5-1 to Example E5-9, Example P5-6 (the ratio of amounts of substances: 16.2) that showed a relatively high water absorption ratio among Example P5-1 to Example P5-10, and Comparative Example C5-1. Table 15 shows measurement results in a dried state, and Table 16 shows measurement results in a water-absorbed state. Meanwhile, freeze drying was applied to both of Example E5-5 and Example P5-6 shown in Tables 15 and 16. As can be understood by referring to Tables 6 and 7, these crosslinked cellulose sheets are polymer sheets each having a low bulk density.

TABLE 15

| Sample | Cross-linking reagent | Ratio of amounts of substances | Drying method | Dried state |||
|---|---|---|---|---|---|---|
| | | | | Elastic modulus (GPa) | Tensile strength (MPa) | Elongation (%) |
| Example E5-5 | EGDE | 3.10 | Freeze drying | 0.251 ± 0.034 | 5.75 ± 0.78 | 5.32 ± 0.78 |
| Example P5-6 | PEDE | 16.20 | Freeze drying | 0.456 ± 0.012 | 3.01 ± 0.15 | 4.04 ± 0.78 |
| Comparative Example C5-1 | — | — | Freeze drying | 0.151 ± 0.021 | 3.75 ± 0.45 | 4.62 ± 0.33 |

TABLE 16

| Sample | Cross-linking reagent | Ratio of amounts of substances | Drying method | Water-absorbed state |||
|---|---|---|---|---|---|---|
| | | | | Elastic modulus (GPa) | Tensile strength (MPa) | Elongation (%) |
| Example E5-5 | EGDE | 3.10 | Freeze drying | 0.00415 ± 0.0011 | 0.912 ± 0.078 | 41.35 ± 2.28 |
| Example P5-6 | PEDE | 16.20 | Freeze drying | 0.00383 ± 0.0012 | 0.8267 ± 0.012 | 69.35 ± 1.5 |
| Comparative Example C5-1 | — | — | Freeze drying | 0.00398 ± 0.00048 | 0.435 ± 0.027 | 30.75 ± 4.49 |

Reference is made to Table 15. With regard to the samples in a dried state, in the both cases where EGDE and PEDE were used as the cross-linking reagents, the elastic modulus was improved as compared with a cellulose sheet having no crosslinked structure. Reference is made to Table 16. With regard to the samples in a water-absorbed state, in the both cases where EGDE and PEDE were used as the cross-linking reagents, though no significant change of the elastic modulus was observed, the tensile strength and elongation were improved as compared with a cellulose sheet having no crosslinked structure. From Tables 13 to 16, it can be understood that in the both cases where EGDE and PEDE were used as the cross-linking reagents, effects of improving the tensile strength and elongation were exhibited by the formation of the crosslinked structure.

Example E11

A crosslinked cellulose sheet of Example E11 was prepared in the same manner as Example E1-1 except that cellulose having a weight-average molecular weight of 105,000 was used as cellulose to be dissolved in the ionic liquid, and the ratio of amounts of substances was made to be 6.0.

Example P11

A crosslinked cellulose sheet of Example P11 was prepared in the same manner as Example P1-1 except that cellulose having a weight-average molecular weight of 105,000 was used as cellulose to be dissolved in the ionic liquid, and the ratio of amounts of substances was made to be 6.0.

Example E12

A crosslinked cellulose sheet of Example E12 was prepared in the same manner as Example E11 except that freeze drying was applied instead of vacuum drying in the step of drying the crosslinked gel.

Example P12

A crosslinked cellulose sheet of Example P12 was prepared in the same manner as Example P11 except that freeze drying was applied instead of vacuum drying in the step of drying the crosslinked gel.

Comparative Example Ce11

A crosslinked carboxymethyl cellulose sheet of Comparative Example Ce11 was prepared in accordance with a method described in PTL 1. Specifically, first, 3.0 g (13.3 mmol) of a sodium salt of carboxymethyl cellulose (CMC) having a degree of substitution of 0.75, and a weight-average molecular weight of 118,050 was dissolved in 100 mL of a 100 mM aqueous solution of sodium hydroxide, and then a solution in which 13.9 g of EGDE corresponding to an amount of substance (79.8 mmol) of 6.0 times the amount of substance of the CMC sodium salt in terms of glucose residue was dissolved was prepared.

Next, the above-described solution was applied on a glass substrate to form a liquid film on the surface of the substrate. The CMC sodium salt and EGDE were made to react in a state that a temperature was kept at 60° C. by a hot water bath for 6 hours to obtain a crosslinked gel. Thereafter, the crosslinked gel was washed with running water until the crosslinked gel became neutral, and the crosslinked gel after washing was subjected to vacuum drying (0.02 MPa, equal to or longer than 2 hours) while being heated to 70° C. After that, a membrane remaining on the substrate was peeled off to obtain a crosslinked CMC sheet of Comparative Example Ce11.

Comparative Example Cp11

A crosslinked CMC sheet of Comparative Example Cp11 was prepared in the same manner as Comparative Example Ce11 except that PEDE was used instead of EGDE. Meanwhile, in preparing a solution of CMC sodium salt, 39.9 g of PEDE corresponding to an amount of substance (79.8 mmol) of 6.0 times the amount of substance of the CMC sodium salt in terms of glucose residue was used.

Comparative Example Ce12

A crosslinked CMC sheet of Comparative Example Ce12 was prepared in the same manner as Comparative Example Ce11 except that freeze drying was applied instead of vacuum drying in the step of drying the crosslinked gel. In freeze drying, the crosslinked gel after washing was immersed in tert-butyl alcohol.

Comparative Example Cp12

A crosslinked CMC sheet of Comparative Example Cp12 was prepared in the same manner as Comparative Example Cp11 except that freeze drying was applied instead of vacuum drying in the step of drying the crosslinked gel. In freeze drying, the crosslinked gel after washing was immersed in tert-butyl alcohol.

Table 17 below shows methods for drying the crosslinked gels, the thicknesses d and the bulk densities $d_B$ of cellulose sheets obtained in the same manner as the sample of Example E1-1, relating to each sample of Example E11, Example P11, Example E12, Example P12, Comparative Example Ce11, Comparative Example Cp11, Comparative Example Ce12 and Comparative Example Cp12 in combination.

TABLE 17

| Sample | Drying method | Thickness d (μm) | Bulk density $d_B$ (g/cm$^3$) |
|---|---|---|---|
| Example E11 | Vacuum drying | 17 | 1.5 |
| Example P11 | Vacuum drying | 16 | 1.5 |
| Example E12 | Freeze drying | 265 | 0.17 |
| Example P12 | Freeze drying | 272 | 0.16 |
| Comparative Example Ce11 | Vacuum drying | 20 | 1.6 |
| Comparative Example Cp11 | Vacuum drying | 19 | 1.6 |
| Comparative Example Ce12 | Freeze drying | 278 | 0.22 |
| Comparative Example Cp12 | Freeze drying | 265 | 0.24 |

Tables 18 and 19 below show the results of tensile testing relating to each sample shown in Table 17. Meanwhile, in Table 19, "N/A" shows that the sample became hydrogel, and the measurement was impossible.

TABLE 18

| Sample | Cross-linking reagent | Ratio of amounts of substances | Dried state Elastic modulus (GPa) | Tensile strength (MPa) | Elongation (%) |
|---|---|---|---|---|---|
| Example E11 | EGDE | 6.00 | 5.0 ± 0.7 | 108.0 ± 5.2 | 5.6 ± 1.1 |
| Comparative Example Ce11 | EGDE | 6.00 | 0.29 ± 0.04 | 2.9 ± 0.1 | 6.46 ± 0.54 |
| Example P11 | PEDE | 6.00 | 4.8 ± 0.6 | 116.0 ± 7.4 | 4.7 ± 1.0 |
| Comparative Example Cp11 | PEDE | 6.00 | 0.23 ± 0.03 | 3.2 ± 0.2 | 5.1 ± 0.3 |
| Example E12 | EGDE | 6.00 | 0.23 ± 0.02 | 4.9 ± 0.8 | 4.7 ± 0.7 |
| Comparative Example Ce12 | EGDE | 6.00 | 0.072 ± 0.005 | 0.42 ± 0.08 | 3.5 ± 1.1 |
| Example P12 | PEDE | 6.00 | 0.24 ± 0.01 | 4.3 ± 0.8 | 4.8 ± 0.6 |
| Comparative Example Cp12 | PEDE | 6.00 | 0.059 ± 0.006 | 0.52 ± 0.27 | 5.1 ± 0.7 |

TABLE 19

| Sample | Cross-linking reagent | Ratio of amounts of substances | Water-absorbed state | | |
| --- | --- | --- | --- | --- | --- |
| | | | Elastic modulus (GPa) | Tensile strength (MPa) | Elongation (%) |
| Example E11 | EGDE | 6.00 | 0.13 ± 0.02 | 7.5 ± 0.8 | 14.3 ± 0.2 |
| Comparative Example Ce11 | EGDE | 6.00 | N/A | N/A | N/A |
| Example P11 | PEDE | 6.00 | 0.21 ± 0.01 | 6.6 ± 0.5 | 15.6 ± 1.1 |
| Comparative Example Cp11 | PEDE | 6.00 | N/A | N/A | N/A |
| Example E12 | EGDE | 6.00 | 0.0065 ± 0.001 | 0.76 ± 0.08 | 29.5 ± 3.5 |
| Comparative Example Ce12 | EGDE | 6.00 | N/A | N/A | N/A |
| Example P12 | PEDE | 6.00 | 0.0048 ± 0.0010 | 0.69 ± 0.06 | 55.6 ± 4.0 |
| Comparative Example Cp12 | PEDE | 6.00 | N/A | N/A | N/A |

From Table 18, it can be understood that when cellulose having about the same weight-average molecular weight was used and the ratios of amounts of substances were made to be the same, the crosslinked cellulose sheet of the present disclosure was capable of exhibiting the elastic modulus and tensile strength that are higher by one or two digits as compared with the CMC sheet in a dried state. In addition, as can be understood from Table 19, the CMC sheet of each Comparative Example was not capable of maintaining the form as a sheet in a water-absorbed state, and therefore, it was impossible to carry out the tensile testing. As described above, a conventional crosslinked cellulose sheet composed of derivatized cellulose was poor in mechanical strengths, and was not suitable for practical use. On the other hand, according to the embodiment of the present disclosure, a crosslinked cellulose sheet that is capable of maintaining the form as a sheet even in a water-absorbed state can be provided.

INDUSTRIAL APPLICABILITY

According to the embodiment of the present disclosure, it is possible to obtain a crosslinked cellulose without derivatization of cellulose. Since the obtained polymer exhibits high water absorbency, the polymer is applicable to various use in the same manner as a conventional water absorptive polymer. For example, the obtained polymer can be utilized for sanitary goods, the representative example of which is a diaper, deodorants, and aromatics, soil improvement additives for improving the water holding property or the like, and the like. In addition, according to the embodiment of the present disclosure, a polymer sheet that is capable of maintaining the form as a sheet even in a water-absorbed state can be provided. Such a self-supporting type polymer sheet can be applied for water absorbing sheets for agricultural, industrial use or the like, distribution materials (cushioning materials) (packing materials), separators of biofuel cells that use biomass ethanol and the like as fuels, cosmetic water retaining face masks, makeup removing sheets, cosmetic pads, bedsore preventing sheets, sweat absorbing sheets and the like, and it is easy to carry and easy to dispose by being removed from a product. Further, the polymer sheet of the present disclosure can be also utilized as, for example, a skin protective film, a skin care film or the like for the purpose of cosmetic or medical use. Furthermore, it is also possible to make the polymer sheet retain, for example, an ingredient that acts on a living body or that protects a living body such as a cosmetic ingredient and to apply colors or patterns and the like, and therefore, the polymer sheet of the present disclosure can be also utilized as, for example, a protective or decorative functional sheet in addition to a cosmetic or medical sheet. Cellulose is a biocompatible material, and therefore, the polymer of the present disclosure can be also applied for carriers for drug delivery systems (DDS), compresses, topical styptic sheets, detection sheets for detecting a substance derived from a living body and the like.

REFERENCE SIGNS LIST

100: polymer
100A, 100B: laminated sheet
100S, 100Sa, 100Sb: polymer sheet
101, 102: protective layer
110: covering material
120: covering material
170: cosmetic ingredient
200A: water absorption body
200B: pack
301: liquid
302: cream

The invention claimed is:
1. A polymer sheet formed of a polymer, wherein
the polymer has a structure in which cellulose substantially represented by the following formula (c1) is crosslinked with a polyfunctional epoxy compound:

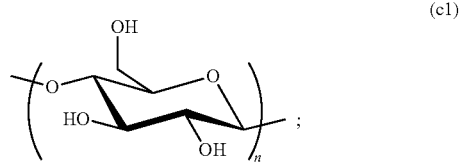

(c1)

in the formula (c1), n represents an integer of not less than 2; and
a crosslinking point carbon ratio calculated based on a peak area included in a spectrum obtained by a solid state $^{13}$C-NMR is not less than 9% and not more than 13%;
the polymer sheet has tensile strength of not less than 3 MPa and not more than 138 MPa in a dried state; and
the polymer sheet has tensile strength of not less than 0.8 MPa and not more than 23 MPa in a water-absorbed state.

2. The polymer sheet according to claim 1, wherein the polyfunctional epoxy compound is a diepoxy compound represented by the following formula (c2):

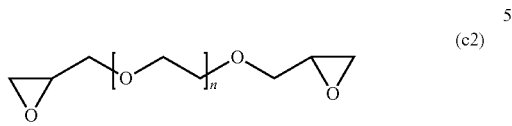

(c2)

wherein in the formula (c2), n represents an integer of not less than 1.

3. The polymer sheet according to claim 1, having the structure in which the cellulose is crosslinked with the polyfunctional epoxy compound at a position of at least one carbon atom selected from the group consisting of 2-position, 3-position, and 6-position carbon atoms included in a beta glucose unit included in the cellulose represented by the formula (c1).

4. The polymer sheet according to claim 1, which has a bulk density of more than 0 g/cm$^3$ and not more than 0.9 g/cm$^3$.

5. A water absorption body comprising:
the polymer sheet according to claim 1; and
a covering material storing the polymer sheet inside, the covering material being water permeable.

6. The polymer sheet according to claim 1, wherein
the polymer sheet has a water absorption ratio of not less than 1,432% and not more than 1,835%.

* * * * *